US012569892B2

(12) United States Patent
Maenle et al.

(10) Patent No.: US 12,569,892 B2
(45) **Date of Patent: *Mar. 10, 2026**

(54) METHODS AND COMPOSITIONS FOR DECONTAMINATING PD CATHETERS

(71) Applicants: Baxter International Inc., Deerfield, IL (US); Baxter Healthcare SA, Glattpark (CH)

(72) Inventors: Garrick Lawrence Maenle, Arlington Heights, IL (US); Robert Radford, Evanston, IL (US); Cristian Adolfo Menzel Bueno, Gurnee, IL (US); Mark Edward Pasmore, Grayslake, IL (US); Shawn Collin Oppegard, Fox River Grove, IL (US)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 158 days.

This patent is subject to a terminal disclaimer.

(21) Appl. No.: 18/214,182

(22) Filed: Jun. 26, 2023

(65) Prior Publication Data

US 2024/0017303 A1      Jan. 18, 2024

Related U.S. Application Data

(63) Continuation-in-part of application No. 17/867,053, filed on Jul. 18, 2022, now Pat. No. 12,420,317.

(51) Int. Cl.
B08B 9/032        (2006.01)
A61M 1/28        (2006.01)
(Continued)

(52) U.S. Cl.
CPC ........... B08B 9/0321 (2013.01); A61M 1/285 (2013.01); C11D 1/37 (2013.01); C11D 3/2086 (2013.01); C11D 3/48 (2013.01); A61M 2025/0019 (2013.01); B08B 2209/032 (2013.01); C11D 1/143 (2013.01); C11D 1/146 (2013.01)

(58) Field of Classification Search
None
See application file for complete search history.

(56) References Cited

U.S. PATENT DOCUMENTS

2017/0157311 A1*  6/2017  Egley ................... A61M 3/0201
2018/0185410 A1*  7/2018  Holmgren .............. A61K 33/04
2019/0336714 A1*  11/2019  Vazales .................. A61B 1/122

* cited by examiner

*Primary Examiner* — Kaj K Olsen
*Assistant Examiner* — Pradhuman Parihar
(74) *Attorney, Agent, or Firm* — K&L Gates LLP

(57) ABSTRACT

A method of performing peritoneal dialysis (PD), the method comprising: delivering a PD fluid to the peritoneal cavity of a patient through a PD catheter; dwelling the PD fluid within the peritoneal cavity; and while dwelling the PD fluid, removing a biofilm from the PD catheter wall using a biofilm removing solution. The biofilm removing solution comprises: sodium citrate dihydrate; citric acid anhydrous; sodium lauryl sulfate; and water. In another aspect, a method for decontaminating a peritoneal dialysis (PD) catheter and removing a biofilm from the PD catheter and a transfer set, the method comprising: providing a biofilm removing solution; transferring the biofilm removing solution into a syringe; connecting the syringe to a transfer set of the PD catheter; and filling the transfer set and the PD catheter with the biofilm removing solution.

22 Claims, 11 Drawing Sheets

(51) Int. Cl.

| | |
|---|---|
| *C11D 1/14* | (2006.01) |
| *C11D 1/37* | (2006.01) |
| *C11D 3/20* | (2006.01) |
| *C11D 3/48* | (2006.01) |
| *A61M 25/00* | (2006.01) |

METHODS AND COMPOSITIONS FOR DECONTAMINATING PD CATHETERS

CROSS-REFERENCE TO RELATED APPLICATIONS

The present application claims priority to U.S. patent application Ser. No. 17/867,053, filed on Jul. 18, 2022, the disclosure of which is incorporated herein by reference for all purposes.

BACKGROUND

The present disclosure relates generally to peritoneal dialysis (PD) treatments and more specifically to the patient's indwelling PD catheter. PD is a renal failure therapy used to treat patients with reduced kidney function. PD is usually performed by the patient, at home, under aseptic conditions. The PD procedure involves the filling of a PD fluid into the peritoneal cavity of a patient via a permanent peritoneal catheter. The PD fluid dwells within the patient for a period of time and is then removed from the patient's peritoneal cavity, in turn removing waste, toxins and excess water from the patient. The patient's peritoneal cavity is typically able to hold 1.5 L to 3 L of the PD fluid. The amount of time the PD fluid remains within the patient's peritoneal cavity is referred to as dwell time, which may be in the order of multiple hours or longer depending on the type of PD fluid. The patient's peritoneal membrane lines the highly vascularized abdominal viscera and therefore acts as a semipermeable membrane across which diffusion (toxin removal) and ultrafiltration (extra water removal) occur. Waste, toxins and excess water are removed from the blood across the peritoneum via diffusion and ultrafiltration.

Several treatment choices are available for patients considering PD: automated peritoneal dialysis (APD) and continuous ambulatory peritoneal dialysis (CAPD). CAPD involves the patient or caregiver manually performing PD fluid exchanges, e.g., three times a day (each lasting 4 to 6 hours) and perhaps once overnight (lasting 8 to 10 hours). The APD system provides an automated cycler that performs PD fluid exchanges, either as continuous cycling PD, tidal PD, or nightly intermittent PD. APD treatments occur typically at night while the patient sleeps, wherein the cycler performs multiple fill, dwell and drain sequences over the course of an 8 to 10 hour treatment.

For both CAPD and APD, the patient is fitted with an indwelling PD catheter, that is semi-permanent and remains with the patient over multiple treatments. Prior to either a CAPD or APD treatment, the patient aseptically connects a patient line of the treatment set to an exposed end of the indwelling PD catheter. A transfer set is typically provided, which resides between the PD catheter and the patient line to aid in the aseptic connection. The indwelling PD catheters can form biofilms on the inner surface of the catheter that may be difficult to remove, creating a reservoir for infectious microorganism leading to relapsing peritonitis, and potentially require catheter removal. Needed in the art is a way to defeat the biofilm, so that antibiotics used in standard peritonitis treatment are able to more effectively kill bacteria in the catheter and to prevent relapsing peritonitis.

SUMMARY

Current methods for killing bacteria formed on the patient's indwelling PD catheter includes intraperitoneal antibiotics delivered through the catheter. Some clinics will lock the catheter with either antibiotics solutions, heparin or tissue Plasminogen Activator (TPA) solutions. Heparin and TPA are used, respectively to prevent the formation and breakup fibrin which can be trapped in the catheter. Antibiotic catheter lock solutions are also commonly used in central venous line catheters as an infection prevention. However, Heparin and TPA target fibrin not biofilm. Antibiotic lock solutions kill bacteria but are not able to penetrate into mature biofilms shielding the bacteria from the antibiotic, nor are they able to aid in the physical removal or breakdown of the biofilm.

Disclosed herein are methods and compositions for decontaminating PD catheters by removing biofilm on the inner wall and/or the external wall (of the portion residing within the patient) of the PD catheter. By disrupting the biofilm, the methods and compositions allow intraperitoneal antibiotics to reach the bacteria. By disrupting the biofilm, the treatment can allow antibiotics used during or subsequent to a standard peritonitis treatment to more effectively kill bacteria in the PD catheter and to prevent relapsing peritonitis. The present disclosure in one embodiment provides a prefilled syringe or similar device to deliver the biofilm removal solution of the present disclosure to the inner lumen of the PD catheter. The biofilm removal solution then dwells, while antibiotics in the peritoneum are also dwelling, and is then flushed out with PD effluent to drain. The present method in one embodiment includes filling patient with PD fluid dosed with antibiotics, locking the catheter with the biofilm solution, dwelling the PD fluid, biofilm solution and antibiotics within the patient's peritoneal cavity, and then draining patient, flushing each fluid out through the PD catheter, including the biofilm microorganisms.

In light of the disclosure set forth herein, and without limiting the disclosure in any way, in a first aspect of the present disclosure, which may be combined with any other embodiment or aspect, or portion thereof, a method of performing peritoneal dialysis (PD) includes delivering a PD fluid to the peritoneal cavity of a patient through a PD catheter; dwelling the PD fluid within the peritoneal cavity; and while dwelling the PD fluid, removing a biofilm from the PD catheter wall using a biofilm removing solution.

In one embodiment, which may be combined with any other embodiment or aspect, or portion thereof, the biofilm removing solution comprises: sodium citrate dihydrate; citric acid anhydrous; alkyl sulfonate such as metallauryl sulfate; and water.

In one embodiment, which may be combined with any other embodiment or aspect, or portion thereof, the biofilm removing solution comprises: sodium citrate dihydrate in a concentration range of about 32.13 g/L to about 39.27 g/L; citric acid anhydrous in a concentration range of about 29.25 g/L to about 35.75 g/L; alkyl sulfonate such as metallauryl sulfate in a concentration range of about 0.95 g/L to about 1.05 g/L; and water.

In one embodiment, which may be combined with any other embodiment or aspect, or portion thereof, the biofilm removing solution further comprises: a pH value in the range of about 3.70 to about 4.10; a total citrates in a concentration range of about 57.45 g/L to about 70.21 g/L; and a specific gravity in range of about 1.025 to about 1.042.

In one embodiment, which may be combined with any other embodiment or aspect, or portion thereof, the biofilm removing solution further comprises: alkyl sulfonates in a concentration range of about 0.61 g/L to about 1.10 g/L.

In one embodiment, which may be combined with any other embodiment or aspect, or portion thereof, the biofilm removing solution further comprises an antimicrobial ingredient.

In one embodiment, which may be combined with any other embodiment or aspect, or portion thereof, the antimicrobial ingredient is selected from the group consisting of: an antibiotic, silver sulfadiazine, a bleach such as a bleach comprising sodium hypochlorite and/or hydrogen peroxide.

In one embodiment, which may be combined with any other embodiment or aspect, or portion thereof, the PD fluid further includes an antibiotic for treating bacteria exposed by the removed biofilm.

In one embodiment, which may be combined with any other embodiment or aspect, or portion thereof, the step of removing the biofilm from the PD catheter wall using the biofilm removing solution comprises: transferring the biofilm removing solution into a syringe; fluidly communicating the syringe with a transfer set located along the PD catheter; and filling the transfer set and the PD catheter with the biofilm removing solution.

In one embodiment, which may be combined with any other embodiment or aspect, or portion thereof, the step of removing the biofilm from the PD catheter wall using the biofilm removing solution further comprises: closing transfer set valve to keep the biofilm removing solution in the transfer set and the PD catheter for a first period of duration.

In one embodiment, which may be combined with any other embodiment or aspect, or portion thereof, the first period of time is between about 1 hours and about 12 hours.

In one embodiment, which may be combined with any other embodiment or aspect, or portion thereof, the first period of time is between about 1 hours and about 1.8 hours.

In one embodiment, which may be combined with any other embodiment or aspect, or portion thereof, the first period of time is about 1.5 hours.

In one embodiment, which may be combined with any other embodiment or aspect, or portion thereof, the step of removing a biofilm from the PD catheter wall using the biofilm removing solution further comprises removing the biofilm removing solution, the PD fluid and the biofilm.

In one embodiment, which may be combined with any other embodiment or aspect, or portion thereof, the step of removing the biofilm removing solution, the PD fluid and the biofilm comprises: replacing the syringe with appropriate fluid connection(s) to an effluent bag or other drain; and opening the transfer set valve to drain the biofilm removing solution and the PD fluid into the effluent bag or other drain via gravity or pumping, wherein the biofilm removing solution and the PD fluid comprise the biofilm removed from the transfer set and the PD catheter.

In one embodiment, which may be combined with any other embodiment or aspect, or portion thereof, the biofilm is removed from the inner walls of the transfer set and the PD catheter and an outer wall of a portion of the PD catheter located within a patient's peritoneal cavity.

In a second aspect of the present disclosure, which may be combined with any other embodiment or aspect, or portion thereof, a method for decontaminating a peritoneal dialysis (PD) catheter and removing a biofilm from the PD catheter and a transfer set includes providing a biofilm removing solution; transferring the biofilm removing solution into a syringe; fluidly communicating the syringe to a transfer set located along the PD catheter; and filling the transfer set and the PD catheter with the biofilm removing solution.

In one embodiment, which may be combined with any other embodiment or aspect, or portion thereof, the method further comprises: closing a transfer set valve to keep the biofilm removing solution in the transfer set and the PD catheter for a first period of duration.

In one embodiment, which may be combined with any other embodiment or aspect, or portion thereof, the first period of time is between about 1 hours and about 12 hours.

In one embodiment, which may be combined with any other embodiment or aspect, or portion thereof, the first period of time is between about 1 hours and about 1.8 hours.

In one embodiment, which may be combined with any other embodiment or aspect, or portion thereof, the first period of time is about 1.5 hours.

In one embodiment, which may be combined with any other embodiment or aspect, or portion thereof, the method further comprises removing the biofilm removing solution, the PD fluid and the biofilm.

In one embodiment, which may be combined with any other embodiment or aspect, or portion thereof, the step of removing the biofilm removing solution, the PD fluid and the biofilm comprises: replacing the syringe with appropriate fluid connection(s) to an effluent bag or other drain; and opening the transfer set valve to drain the biofilm removing solution and the PD fluid into the effluent bag via gravity or pumping, wherein the biofilm removing solution and the PD fluid comprise the biofilm removed from the transfer set and the PD catheter.

In one embodiment, which may be combined with any other embodiment or aspect, or portion thereof, the biofilm is removed from the inner walls of the transfer set and the PD catheter and an outer wall of a portion of the PD catheter located within a patient's peritoneal cavity.

In one embodiment, which may be combined with any other embodiment or aspect, or portion thereof, the biofilm removing solution comprises: sodium citrate dihydrate; citric acid anhydrous; alkyl sulfonate such as metal lauryl sulfate (e.g., sodium lauryl sulfate); and water.

In one embodiment, which may be combined with any other embodiment or aspect, or portion thereof, the biofilm removing solution comprises: sodium citrate dihydrate in a concentration range of about 32.13 g/L to about 39.27 g/L; citric acid anhydrous in a concentration range of about 29.25 g/L to about 35.75 g/L; alkyl sulfonate such as metal lauryl sulfate (e.g., sodium lauryl sulfate) in a concentration range of about 0.95 g/L to about 1.05 g/L; and water.

In one embodiment, which may be combined with any other embodiment or aspect, or portion thereof, the biofilm removing solution further comprises: a pH value in the range of about 3.70 to about 4.10; a total citrates in a concentration range of about 57.45 g/L to about 70.21 g/L; and a specific gravity in range of about 1.025 to about 1.042.

In one embodiment, which may be combined with any other embodiment or aspect, or portion thereof, the biofilm removing solution further comprises: alkyl sulfonates in a concentration range of about 0.61 g/L to about 1.10 g/L.

In one embodiment, which may be combined with any other embodiment or aspect, or portion thereof, the biofilm removing solution further comprises an antimicrobial ingredient.

In one embodiment, which may be combined with any other embodiment or aspect, or portion thereof, the antimicrobial ingredient is selected from the group consisting of an antibiotic, a bleach and silver sulfadiazine.

In one embodiment, which may be combined with any other embodiment or aspect, or portion thereof, the PD fluid further includes an antibiotic for treating bacteria exposed by the removed biofilm.

In a third aspect of the present disclosure, which may be combined with any other embodiment aspect, or portion thereof, a method of performing peritoneal dialysis (PD) includes pumping delivering a PD fluid including a biofilm removing solution to the peritoneal cavity of a patient through a PD catheter; dwelling the PD fluid including a biofilm removing solution within the peritoneal cavity; and while dwelling the PD fluid including a biofilm removing solution, removing a biofilm from the PD catheter wall via the a biofilm removing solution.

In one embodiment, which may be combined with any other embodiment or aspect, or portion thereof, the PD fluid further includes an antibiotic for treating bacteria exposed by the removed biofilm.

In a fourth aspect of the present disclosure, which may be combined with any other embodiment or aspect, or portion thereof, a composition for decontaminating a peritoneal dialysis (PD) catheter and removing a biofilm from the PD catheter and a transfer set includes sodium citrate dihydrate; citric acid anhydrous; a surfactant; and water.

In one embodiment, which may be combined with any other embodiment or aspect, or portion thereof, the surfactant is selected from the group consisting of a rhamnolipid, fengycin, a glycolipid, a lipopeptide, a poloxamer, a betaine, alkyl sulfonate such as metal lauryl sulfate (e.g., sodium lauryl sulfate), sodium dodecyl sulfate, and cetyl trimethyl ammonium bromide.

In one embodiment, which may be combined with any other embodiment or aspect, or portion thereof, the surfactant is sodium lauryl sulfate.

In one embodiment, which may be combined with any other embodiment or aspect, or portion thereof, the composition comprises: sodium citrate dihydrate in a concentration range of about 32.13 g/L to about 39.27 g/L; citric acid anhydrous in a concentration range of about 29.25 g/L to about 35.75 g/L; alkyl sulfonate such as metal lauryl sulfate (e.g., sodium lauryl sulfate) in a concentration range of about 0.95 g/L to about 1.05 g/L; and water.

In one embodiment, which may be combined with any other embodiment or aspect, or portion thereof, the composition comprises: sodium citrate dihydrate in a concentration of about 35 g/L; citric acid anhydrous in a concentration of about 33 g/L; alkyl sulfonate such as metal lauryl sulfate (e.g., sodium lauryl sulfate) in a concentration of about 1 g/L; and water.

In one embodiment, which may be combined with any other embodiment or aspect, or portion thereof, the composition further comprises: a total citrates in a concentration range of about 57.45 g/L to about 70.21 g/L, wherein a biofilm removing solution comprising the composition has a specific gravity in a range of about 1.025 to about 1.042 and has a pH value in the range of about 3.70 to about 4.10.

In one embodiment, which may be combined with any other embodiment or aspect, or portion thereof, the composition further comprises: alkyl sulfonates in a concentration range of about 0.61 g/L to about 1.10 g/L.

In one embodiment, which may be combined with any other embodiment or aspect, or portion thereof, the composition comprises: sodium citrate dihydrate in a concentration of about 35 g/L; citric acid anhydrous in a concentration of about 33 g/L; alkyl sulfonate such as metal lauryl sulfate (e.g., sodium lauryl sulfate) in a concentration of about 1 g/L; water; a total citrates in a concentration of about 63.83 g/L; and alkyl sulfonates in a concentration range of about 1.00 g/L, wherein a biofilm removing solution comprising the composition has a specific gravity in range of about 1.033 and has a pH value of about 3.93.

In one embodiment, which may be combined with any other embodiment or aspect, or portion thereof, the composition further comprises an antimicrobial ingredient.

In one embodiment, which may be combined with any other embodiment or aspect, or portion thereof, the antimicrobial ingredient is selected from the group consisting of an antibiotic, a bleach and silver sulfadiazine.

In a fifth aspect of the present disclosure, which may be combined with any other embodiment or aspect, or portion thereof, a method of removing at least a portion of a biofilm present in the lumen of an indwelling peritoneal catheter while performing peritoneal dialysis therapy includes delivering a dialysis fluid to the peritoneal cavity of a patient through the catheter; injecting a biofilm removing solution into the lumen of the catheter to occupy at least a portion of the lumen; dwelling the dialysis fluid within the peritoneal cavity; and removing the at least a portion of the biofilm removing solution from the catheter by withdrawing at least a portion of the dialysis fluid from the peritoneal cavity into the catheter.

In one aspect of the present disclosure, which may be combined with any other aspect, or portion thereof, any of the features, functionality and alternatives described in connection with any one or more of FIGS. 1 to 11 may be combined with any of the features, functionality and alternatives described in connection with any other of FIGS. 1 to 11.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DESCRIPTION OF DRAWINGS

As shown in FIG. 1, a permanent PD catheter 1 is inserted into the peritoneal cavity 2 of a patient 3. Through the PD catheter 1, an antibiotic-containing PD fluid 4 is delivered into the peritoneal cavity 2 of the patient 3. A biofilm-removing solution comprising the present composition s injected via a syringe 5 through the PD catheter 1, which attacks and removes or substantially removes the biofilm attached to the inner wall of the PD catheter 1. Numeral 6 shows an example of the inner wall the PD catheter 1 with biofilm 8. Numeral 7 shows an example of the inner wall the PD catheter 1 without biofilm after the PD catheter 1 is injected with the biofilm-removing solution comprising the present composition. FIG. 1 further illustrates that a transfer set 9 including a transfer set valve is provided to enable the patient to allow or block flow through PD catheter 1.

As shown in FIG. 2, a clamp or stop 5s, e.g., threaded or press-fit onto syringe plunger 5p can be used to prevent overfill and to meter a desired or prescribed biofilm-removing solution volume. Clamp or threaded stop 5s may be set using graduated markings on syringe plunger 5p, which match or delineate the prescribed biofilm-removing solution volume.

FIG. 3A and FIG. 3B show microscopy of *P. aeruginosa* biofilm on catheter material (silicone). As shown in FIG. 3B, the biofilm was removed or substantially removed after the wash using Product X as compared to the control without the wash using Product X (FIG. 3A).

In FIG. 4, viable bacteria recovered from catheter material after 6 hours treatment. Log reduction value (LRV) indicates removal of viable organisms. Note: negative LRV indicates growth of organisms during treatment.

In FIG. 5, biomass removal % relative to untreated control for *P. aeruginosa*, recovered from catheter material after 6 hours treatment. Note: negative percentage indicates growth of organisms/biofilm during treatment.

FIGS. 6A, 6B and 6C show that prior to injecting the biofilm removing solution of the present disclosure, the patient's peritoneal cavity 2 is first filled the PD fluid from a PD fluid source 10 to perform a PD treatment exchange. FIG. 6A shows PD fluid located within source 10, while FIG. 6B shows that the PD fluid has been delivered to the patient's peritoneal cavity 2. The patient fill of PD fluid may be performed via automated peritoneal dialysis (APD) or as shown in FIGS. 6A and 6B via continuous ambulatory peritoneal dialysis (CAPD). For APD, the biofilm removing solution may be injected through a sealed septum (not illustrated) provided in transfer set 9, e.g., after the first patient fill. As shown in FIG. 6C, biofilm removing solution is transferred from sterile ampule 11 to an, e.g., 10-20 mL syringe 5 via a luer connector to ready the biofilm removing solution for injection during the dwell of PD fluid in the patient's peritoneal cavity 2.

FIGS. 7A, 7B and 7C show the delivery and dwell of the biofilm removing solution in transfer set 9 and PD catheter 1 and perhaps into the patient's peritoneal cavity 2 to contact the outside of a portion of PD catheter 1 located therein. As shown in FIG. 7A, the Luer-connect solution-containing syringe 5 is connected to PD catheter 1. FIG. 7B shows that when plunger 5b of syringe 5 is pressed, transfer set 9 and PD catheter 1 are filled with, e.g., 5-10 mL, of the biofilm removing solution. FIG. 7C shows that the valve of transfer set 9 remains open and syringe 5 remains in place to aseptically close the biofilm removing solution within transfer set 9 and PD catheter 1 during, e.g., a six hour dwell. In an alternative embodiment, syringe 5 injects the biofilm removing solution directly into transfer set 9 and through PD catheter 1, after which syringe 5 is removed and the valve of transfer set 9 is closed to aseptically seal the biofilm removing solution within transfer set 9 and PD catheter 1 during, e.g., a six hour dwell.

FIGS. 8A, 8B and 8C show the removal of the biofilm removing solution, correspondingly removed biofilm, antibiotic, and used PD fluid after the patient dwell. For example, FIG. 8A shows that syringe 5 is replaced with appropriate fluid connection(s) to one or more used PD fluid or effluent bag 11 (for CAPD, for APD the PD catheter 1 is connected to a patient line leading to a cycler that removes the biofilm removing solution, correspondingly removed biofilm, antibiotic, and used PD fluid). FIG. 8B shows that the valve of transfer set 9 is opened and draining of the PD catheter and the patient's peritoneal cavity 2 may begin either via gravity (CAPD) or pumping (APD). The patient drain in an embodiment removes the biofilm via shear stress and by flushing the detached organisms from the PD catheter. FIG. 8C shows that the patient's peritoneal cavity 2 is drained, wherein biofilm has been correspondingly removed from PD catheter 1 and transfer set 9. PD treatment may continue according to the patient's prescription, wherein the biofilm removing solution may or may not be repeated.

FIG. 9A shows that citric acid of the present disclosure attaches to and removes the metallic bonds that hold the EPS structure together. FIG. 9B shows that the polymers are released and the EPS is dismantled. FIG. 9C shows that sodium splits off from the sodium citrate of the present disclosure. The presence of the citric acid prevents cross-link reformation. The polymers of the EPS take-on a random amorphous confirmation and can be absorbed into solution. It is also contemplated to provide a surfactant to help solubilize the EPS and reduce the chances of the EPS's becoming reattached.

FIGS. 10A and 10B show removal of biofilm and viable bacteria by using the solution. Representative images of *S. aureus* biofilm (48 h) grown on silicone. Green=Live Cells; Red=Dead Cells. As shown in FIG. 10B, the biofilm was removed or substantially removed after the wash of the biofilm removing solution (i.e. Product X) for 6 hours as compared to the untreated control without the wash of the solution (FIG. 10A).

FIG. 11 shows removal of biofilm from silicone. No viable bacteria were recovered after treatment with the solution (i.e., the Product X solution). Controls: untreated, PD fluid (2.5% glucose) and PD fluid w/gentamicin. Treatment: 1 exposure for 6 h.

DETAILED DESCRIPTION

Definitions

Figure 1:
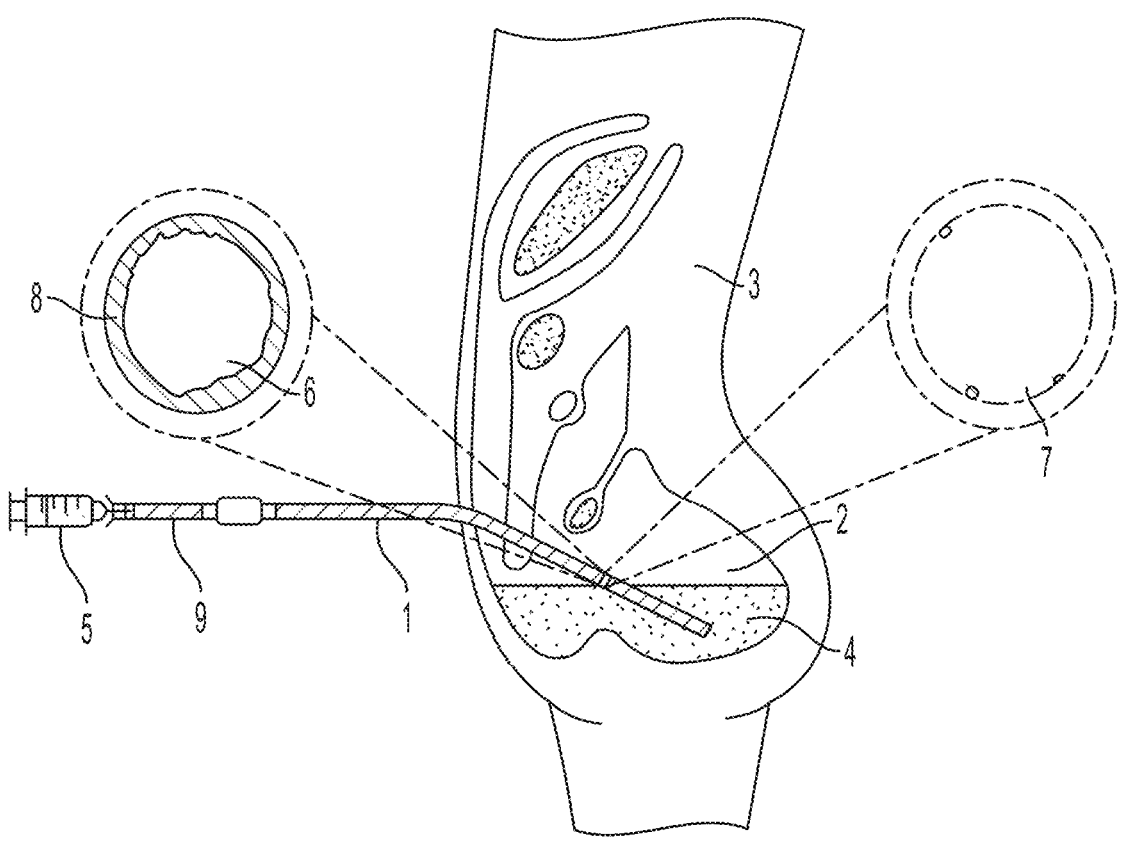
FIG. 1 is a diagram showing an exemplary PD catheter decontamination and biofilm removal according to some embodiments of the present disclosure.

Some definitions are provided hereafter. Nevertheless, definitions may be located in the "Embodiments" section below, and the above header "Definitions" does not mean that such disclosures in the "Embodiments" section are not definitions.

All percentages are by weight of the total weight of the composition unless expressed otherwise. Similarly, all amounts and all ratios are by weight unless expressed otherwise. When reference is made to the pH, values correspond to pH measured at 25° C. with standard equipment. As used herein, "about," "approximately" and "substantially" are understood to refer to numbers in a range of numerals, for example the range of −10% to +10% of the referenced number, preferably –5% to +5% of the referenced number, more preferably –1% to +1% of the referenced number, most preferably –0.1% to +0.1% of the referenced number.

Furthermore, all numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

As used herein and in the appended claims, the singular form of a word includes the plural, unless the context clearly dictates otherwise. Thus, the references "a," "an" and "the" are generally inclusive of the plurals of the respective terms. For example, reference to "an amino acid" or "the amino acid" includes a plurality of such "amino acids." The term "and/or" used in the context of "X and/or Y" should be interpreted as "X," or "Y," or "X and Y." Similarly, "at least one of X or Y" should be interpreted as "X," or "Y," or "both X and Y."

Similarly, the words "comprise," "comprises," and "comprising" are to be interpreted inclusively rather than exclusively. Likewise, the terms "include," "including" and "or" should all be construed to be inclusive, unless such a construction is clearly prohibited from the context. However, the embodiments provided by the present disclosure may lack any element that is not specifically disclosed herein. Thus, a disclosure of an embodiment defined using the term "comprising" is also a disclosure of embodiments "consisting essentially of" and "consisting of" the disclosed components.

Where used herein, the term "example," particularly when followed by a listing of terms, is merely exemplary and illustrative, and should not be deemed to be exclusive or comprehensive. Any embodiment disclosed herein can be combined with any other embodiment disclosed herein unless explicitly indicated otherwise.

As used herein, the term "patient" is understood to include an animal, for example a mammal, and preferably a human that is receiving or intended to receive treatment (e.g., peritoneal dialysis (PD)), as treatment is herein defined. While the terms "individual" and "patient" are often used herein to refer to a human, the present disclosure is not so limited.

Accordingly, the terms "individual" and "patient" refer to any animal, mammal or human that can benefit from the methods and compositions disclosed herein. Indeed, non-human animals may undergo a PD treatment.

The term "elderly" in the context of a human means an age from birth of at least 55 years, preferably above 63 years, more preferably above 65 years, and most preferably above 70 years. The term "older adult" or "ageing individual" in the context of a human means an age from birth of at least 45 years, preferably above 50 years, more preferably above 55 years, and includes elderly individuals.

For other animals, an "older adult" or "ageing individual" has exceeded 50% of the average lifespan for its particular species and/or breed within a species. An animal is considered "elderly" if it has surpassed 66% of the average expected lifespan, preferably if it has surpassed the 75% of the average expected lifespan, more preferably if it has surpassed 80% of the average expected lifespan. An ageing cat or dog has an age from birth of at least about 5 years. An elderly cat or dog has an age from birth of at least about 7 years.

The terms "treatment" and "treating" include any effect that results in the improvement of the condition or disorder, for example lessening, reducing, modulating, or eliminating the condition or disorder. The term does not necessarily imply that a subject is treated until total recovery. Non-limiting examples of "treating" or "treatment of" a condition or disorder include: (1) inhibiting the condition or disorder, i.e., arresting the development of the condition or disorder or its clinical symptoms and (2) relieving the condition or disorder, i.e., causing the temporary or permanent regression of the condition or disorder or its clinical symptoms. A treatment can be patient- or doctor-related.

The term "peritoneal dialysis" or "PD," as used herein, refers to a type of dialysis which uses the peritoneum wall in a person's abdomen as the membrane through which fluid and dissolved substances are exchanged with the blood. PD is used to remove excess fluid, correct electrolyte problems, and remove toxins in those with kidney failure. PD benefits include greater flexibility and better tolerability in those with significant heart disease. In PD, a specific solution (e.g., a PD fluid) is introduced through a permanent tube in the lower abdomen and then removed.

This may either occur at regular intervals throughout the day, known as continuous ambulatory peritoneal dialysis (CAPD), or at night with the assistance of a machine, known as automated peritoneal dialysis (APD). The PD fluid is typically made of sodium chloride, bicarbonate, and an osmotic agent such as glucose.

The term "PD catheter", as used herein, refers to a thin tube made from medical grade materials serving as a medical device that can be inserted into the peritoneal cavity of a patient for peritoneal dialysis or PD. As show in FIG. 1, one end of PD catheter 1 is inserted into the peritoneal cavity of the patient. The other end of PD catheter 1 is connected to transfer set 9, which allows the PD catheter (or transfer set 9) to connect with other devices such as syringe 5 or effluent bag 11.

The term "biofilm," as used herein, refers to any syntrophic consortium of microorganisms in which cells stick to each other and often also to a surface (e.g., the inner or outside wall surface of a PD catheter). These adherent cells become embedded within a slimy extracellular matrix that is composed of extracellular polymeric substances (EPSs). The cells within the biofilm produce the EPS components, which are typically a polymeric conglomeration of extracellular polysaccharides, proteins, lipids and DNA. Because these cells have three-dimensional structure and represent a community lifestyle for microorganisms, they have been metaphorically described as "cities for microbes." In one embodiment, the biofilm is on the inner or outside (portion inside the patient's peritoneal cavity) wall surface of the PD catheter.

The term "peritoneal dialysis fluid" or "PD fluid," as used herein, refers to a specific solution used in the peritoneal dialysis. The PD fluid is usually introduced through a permanent tube in the lower abdomen and then removed. This process may either occur at regular intervals throughout the day, known as continuous ambulatory peritoneal dialysis (CAPD), or at night with the assistance of a machine, known as automated peritoneal dialysis (APD). The PD fluid is typically made of sodium chloride, bicarbonate, and an osmotic agent such as glucose. The PD fluid used for peritoneal dialysis is on the World Health Organization's List of Essential Medicines.

The term "biofilm removing solution," as used herein, refers to a solution comprising the composition of the present disclosure, which is unexpectedly and surprisingly effective for removing the biofilm on a surface. In one embodiment, the biofilm removing solution comprises sodium citrate (e.g., sodium citrate dihydrate); citric acid (e.g., citric acid anhydrous); a surfactant (e.g., sodium lauryl sulfate); and water. In one embodiment, the biofilm is on the inner or outside (portion inside the patient's peritoneal cavity) wall surface of a PD catheter.

Figures 9A, 9B, 9C:
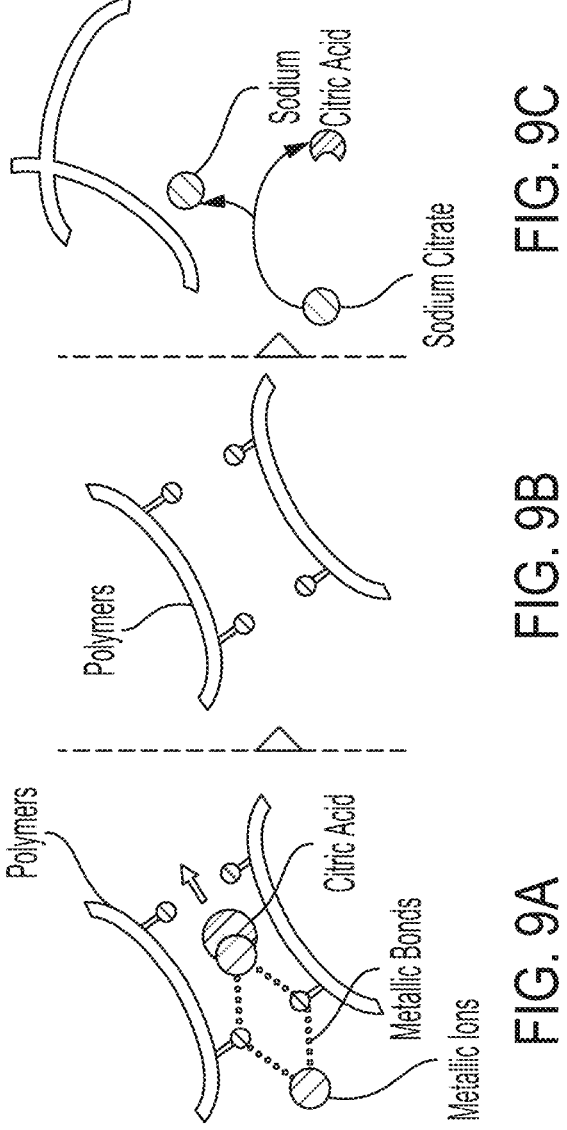
FIGS. 9A, 9B and 9C are a set of diagrams showing the mechanism of the biofilm removal by deconstructing the extracellular polymeric substance (EPS) according to certain embodiments of the present disclosure. For example.

It was surprisingly found that the citric acid of the present disclosure may attach to and remove metallic bonds of extracellular polymeric substances secreted by microorganisms to remove the extracellular polymeric substances of the biofilm, thus removing the biofilm (e.g., FIGS. 9A and 9B). It was further surprisingly found that the citric acid of the present disclosure may prevent further cross-link formation of the extracellular polymeric substances of the biofilm (e.g., FIG. 9C).

The term "surfactant", "detergent" or "surface acting agent", as used herein, refers to any organic compound that is amphiphilic, i.e., containing both hydrophobic groups ("tails") and hydrophilic groups ("heads"), which render surfactants soluble in both organic solvents and water. A surfactant can be classified by the presence of formally charged groups in its head. A non-ionic surfactant has no charge groups in its head, whereas an ionic surfactant carries a net charge in its head. A zwitterionic surfactant contains a head with two oppositely charged groups. Some examples of common surfactants include: Anionic (based on sulfate, sulfonate or carboxylate anions): alkyl sulfonate such as metal lauryl sulfate (e.g., sodium lauryl sulfate; SLS), perfluorooctanoate (PFOA or PFO), perfluorooctanesulfonate (PFOS), sodium dodecyl sulfate (SDS), ammonium lauryl sulfate, and other alkyl sulfate salts, sodium laureth sulfate (also known as sodium lauryl ether sulfate, or SLES), alkyl benzene sulfonate; cationic (based on quaternary ammonium cations): cetyl trimethylammonium bromide (CTAB) a.k.a., hexadecyl trimethyl ammonium bromide, and other alkyltrimethylammonium salts, cetylpyridinium chloride (CPC), polyethoxylated tallow amine (POEA), benzalkonium chloride (BAC), benzethonium chloride (BZT); Zwitterionic (amphoteric): dodecyl betaine; cocamidopropyl betaine; coco ampho glycinate; nonionic: alkyl poly(ethylene oxide), alkylphenol poly(ethylene oxide), copolymers of poly(ethylene oxide) and poly(propylene oxide) (commercially known as Poloxamers or Poloxamines), alkyl polyglucosides, including octyl glucoside, decyl maltoside, fatty alcohols (e.g., cetyl alcohol and oleyl alcohol), cocamide MEA, cocamide DEA, polysorbates (Tween 20, Tween 80, etc.), Triton detergents, and dodecyl dimethylamine oxide.

In one embodiment, the surfactant may include biosurfactants (rhamnolipids, fengycin, glycolipid, lipopeptide, etc.), synthetic (poloxamers and betaines) and natural (sodium lauryl/dodecyl sulfate, cetyl trimethyl ammonium bromide, etc.). In one embodiment, the surfactant is selected from the group consisting of a rhamnolipid, fengycin, a glycolipid, a lipopeptide, a poloxamer, a betaine, sodium lauryl sulfate, sodium dodecyl sulfate, and cetyl trimethyl ammonium bromide. In one exemplary embodiment, the surfactant comprises sodium lauryl sulfate. More preferably, the surfactant is sodium lauryl sulfate.

The term "alkyl sulfonates," as used herein, refers to esters of alkane sulfonic acids with the general formula $R—SO_2—O—R'$ (R and R' are alkanes). Alkyl sulfonates act as alkylating agents, some of them are used as alkylating antineoplastic agents in the treatment of cancer, e.g., Busulfan.

The term "antimicrobial ingredient," as used herein, refers to any agent or ingredient that kills microorganisms or stops their growth. Antimicrobial ingredient can be grouped according to the microorganisms they act primarily against. For example, antibiotics are used against bacteria, and antifungals are used against fungi. They can also be classified according to their function. Agents that kill microbes are microbicides, while those that merely inhibit their growth are called bacteriostatic agents.

The main classes of antimicrobial agents or ingredients are disinfectants (non-selective agents, such as bleach comprising sodium hypochlorite), which kill a wide range of microbes on non-living surfaces to prevent the spread of illness, antiseptics (which are applied to living tissue and help reduce infection during surgery), and antibiotics (which destroy microorganisms within the body). In various embodiments, any other chemicals providing "free chlorine" (which is the active agent in bleach) may also be provided.

The term "antibiotic," as used herein, refers to those formulations derived from living microorganisms and synthetic agents, such as sulfonamides or fluoroquinolones. Antimicrobial agents or ingredients include antibacterials and all antimicrobials. Antibacterial agents may be further subdivided into bactericidal agents, which kill bacteria, and bacteriostatic agents, which slow down or stall bacterial growth.

In one embodiment, the antimicrobial ingredient is selected from the group consisting of an antibiotic, a bleach and silver sulfadiazine.

The term "antibacterials," as used herein, refers to any agents or chemicals for treating bacterial infections. Antibacterials may be classified generally as beta-lactams, macrolides, quinolones, tetracyclines or aminoglycosides.

Embodiments

The Compositions

In an aspect, the present disclosure relates to a composition or a solution (e.g., a biofilm removing solution) comprising the composition for decontaminating peritoneal dialysis (PD) catheters and removing biofilms from the PD catheters. In one embodiment, the composition comprises a metal citrate (e.g., sodium citrate); an acid (e.g., citric acid); a surfactant (e.g., an anionic surfactant); and water.

For example, the metal citrate may comprise sodium citrate. The acid may comprise citric acid. The surfactant may comprise biosurfactants (rhamnolipids, fengycin, glycolipid, lipopeptide, etc.), synthetic (poloxamers and betaines) and natural (sodium lauryl/dodecyl sulfate, cetyl trimethyl ammonium bromide, etc.). In one embodiment, the surfactant is selected from the group consisting of a rhamnolipid, fengycin, a glycolipid, a lipopeptide, a poloxamer, a betaine, sodium lauryl sulfate, sodium dodecyl sulfate, and cetyl trimethyl ammonium bromide. In one exemplary embodiment, the surfactant comprises sodium lauryl sulfate. More preferably, the surfactant is sodium lauryl sulfate.

In one embodiment, the composition comprises sodium citrate (e.g., sodium citrate dihydrate); citric acid (e.g., citric acid anhydrous); a surfactant (e.g., sodium lauryl sulfate); and water.

In one exemplary embodiment, the composition comprises sodium citrate dihydrate; citric acid anhydrous; sodium lauryl sulfate; and water.

It was unexpectedly and surprisingly found that a biofilm removing solution comprising sodium citrate dihydrate, citric acid anhydrous, sodium lauryl sulfate, and water can be used to remove biofilms from inner and external wall surfaces of a device such as a PD catheter.

Furthermore, it was surprisingly found that the citric acid of the present disclosure may attach to and remove metallic bonds of extracellular polymeric substances secreted by microorganisms to remove the extracellular polymeric substances of the biofilm, thus removing the biofilm (e.g., FIGS. 9A and 9B). It was further surprisingly found that the citric acid of the present disclosure may prevent further cross-link formation of the extracellular polymeric substances of the biofilm (e.g., FIG. 9C). In various embodiments, other chelating agents may be provided and used to attach to and remove metallic bonds of extracellular polymeric substances secreted by microorganisms to remove the extracellular polymeric substances of the biofilm, thus removing the biofilm. The other chelating agents may for example include Ethylenediaminetetraacetic Acid (EDTA) and nitrilotriacetic acid (NTA).

FIGS. 9A, 9B and 9C show the potential mechanism of the biofilm removal by deconstructing the extracellular polymeric substance (EPS) of a biofilm according to certain embodiments of the present disclosure. For example, FIG. 9A shows that citric acid of the present disclosure attaches to and removes the metallic bonds that hold the EPS structure together. FIG. 9B shows that the polymers are released and the EPS is dismantled. FIG. 9C shows that sodium splits off from the sodium citrate of the present disclosure. The presence of the citric acid thus prevents cross-link reformation. The polymers of the EPS take-on a random amorphous confirmation and can be absorbed into solution. A surfactant may also be provided, wherein the solubilization of the EPS by the surfactant becomes an important part of the biofilm removal.

In one exemplary embodiment, a composition of the present disclosure comprises sodium citrate dihydrate, citric acid anhydrous, sodium lauryl sulfate, and water.

In one embodiment, the composition comprises sodium citrate dihydrate in a concentration of about 1 g/L to about 100 g/L, about 2 g/L to about 95 g/L, about 3 g/L to about 90 g/L, about 4 g/L to about 85 g/L, about 5 g/L to about 80 g/L, about 6 g/L to about 75 g/L, about 7 g/L to about 70 g/L, about 8 g/L to about 65 g/L, about 9 g/L to about 60 g/L, about 10 g/L to about 55 g/L, about 15 g/L to about 50 g/L, about 20 g/L to about 45 g/L, about 25 g/L to about 43 g/L, about 30 g/L to about 42 g/L, about 31 g/L to about 41 g/L, about 32 g/L to about 40 g/L, or about 32.13 g/L to about 39.27 g/L; citric acid anhydrous in a concentration range of about 1 g/L to about 90 g/L, about 2 g/L to about 80 g/L, about 3 g/L to about 85 g/L, about 4 g/L to about 80 g/L, about 5 g/L to about 75 g/L, about 6 g/L to about 70 g/L, about 7 g/L to about 65 g/L, about 8 g/L to about 60 g/L, about 9 g/L to about 55 g/L, about 10 g/L to about 50 g/L, about 15 g/L to about 45 g/L, about 20 g/L to about 40 g/L, about 25 g/L to about 39 g/L, about 26 g/L to about 38 g/L, about 27 g/L to about 37 g/L, about 28 g/L to about 36 g/L, about 29 g/L to about 35.9 g/L, or about 29.25 g/L to about 35.75 g/L; sodium lauryl sulfate in a concentration range of about 0.01 g/L to about 100 g/L, about 0.02 g/L to about 90 g/L, about 0.03 g/L to about 80 g/L, about 0.04 g/L to about 70 g/L, about 0.05 g/L to about 60 g/L, about 0.06 g/L to about 50 g/L, about 0.07 g/L to about 40 g/L, about 0.08 g/L to about 30 g/L, about 0.09 g/L to about 20 g/L, about 0.10 g/L to about 10 g/L, about 0.2 g/L to about 9 g/L, about 0.3 g/L to about 8 g/L, about 0.4 g/L to about 7 g/L, about 0.5 g/L to about 6 g/L, about 0.6 g/L to about 5 g/L, about 0.7 g/L to about 4 g/L, about 0.8 g/L to about 3 g/L, about 0.85 g/L to about 2 g/L, about 0.9 g/L to about 1.5 g/L, or about 0.95 g/L to about 1.05 g/L; and water.

In one embodiment, the composition comprises sodium citrate dihydrate in a concentration of about 32.13 g/L to about 39.27 g/L; citric acid anhydrous in a concentration range of about 29.25 g/L to about 35.75 g/L; sodium lauryl sulfate in a concentration range of about 0.95 g/L to about 1.05 g/L; and water.

In one exemplary embodiment, the composition comprises sodium citrate dihydrate in a concentration of about 35 g/L; citric acid anhydrous in a concentration of about 33 g/L; sodium lauryl sulfate in a concentration of about 1 g/L; and water.

In one embodiment, a biofilm removing solution comprising the composition has a pH value in the range of about 1 to about 10, about 1.1 to about 9.5, about 1.2 to about 9, about 1.3 to about 8.5, about 1.4 to about 8, about 1.5 to about 7.5, about 1.6 to about 7, about 1.7 to about 6.5, about 1.8 to about 6, about 1.9 to about 5.5, about 2.0 to about 5, about 2.2 to about 4.9, about 2.4 to about 4.8, about 2.6 to about 4.7, about 2.8 to about 4.6, about 3.0 to about 4.5, about 3.2 to about 4.4, about 3.4 to about 4.3, about 3.5 to about 4.25, about 3.6 to about 4.2, or about 3.70 to about 4.10.

In one exemplary embodiment, a biofilm removing solution comprising the composition comprises a pH value of about 3.93.

In one embodiment, the composition further comprises a total citrates in a concentration range of about 1 g/L to about 200 g/L, about 5 g/L to about 160 g/L, about 10 g/L to about 140 g/L, about 15 g/L to about 120 g/L, about 20 g/L to about 100 g/L, about 25 g/L to about 95 g/L, about 30 g/L to about 90 g/L, about 35 g/L to about 85 g/L, about 40 g/L to about 80 g/L, about 45 g/L to about 75 g/L, about 50 g/L to about 74 g/L, about 51 g/L to about 73 g/L, about 52 g/L to about 72 g/L, about 53 g/L to about 71.5 g/L, about 54 g/L to about 71 g/L, about 55 g/L to about 70.9 g/L, about 56 g/L to about 70.8 g/L, about 56.5 g/L to about 70.7 g/L, about 57 g/L to about 70.6 g/L, about 57.2 g/L to about 70.4 g/L, or about 57.45 g/L to about 70.21 g/L.

In one exemplary embodiment, the composition further comprises a total citrates in a concentration of about 63.83 g/L.

In one embodiment, a biofilm removing solution comprising the composition has a specific gravity in a range of about 1.0 to about 1.2, about 1.005 to about 1.1, about 1.006 to about 1.085, about 1.007 to about 1.080, about 1.008 to about 1.075, about 1.010 to about 1.070, about 1.015 to about 1.065, about 1.020 to about 1.060, about 1.021 to about 1.055, about 1.022 to about 1.050, about 1.023 to about 1.045, about 1.022 to about 1.043, or about 1.025 to about 1.042.

In one exemplary embodiment, a biofilm removing solution comprising the composition has a specific gravity of about 1.033.

In one embodiment, the composition further comprises a total citrates in a concentration range of about 57.45 g/L to about 70.21 g/L, and a biofilm removing solution comprising the composition has a specific gravity in a range of about 1.025 to about 1.042 and has a pH value in the range of about 3.70 to about 4.10.

In one embodiment, the composition further comprises alkyl sulfonates in a concentration range of about 0.1 g/L to about 10 g/L, about 0.15 g/L to about 9 g/L, about 0.2 g/L to about 8 g/L, about 0.25 g/L to about 7 g/L, about 0.3 g/L to about 6 g/L, about 0.35 g/L to about 5 g/L, about 0.4 g/L to about 4 g/L, about 0.45 g/L to about 3 g/L, about 0.5 g/L to about 2 g/L, about 0.51 g/L to about 1.9 g/L, about 0.52 g/L to about 1.8 g/L, about 0.53 g/L to about 1.7 g/L, about 0.54 g/L to about 1.6 g/L, about 0.55 g/L to about 1.5 g/L, about 0.57 g/L to about 1.4 g/L, about 0.59 g/L to about 1.3 g/L, about 0.60 g/L to about 1.2 g/L or about 0.61 g/L to about 1.10 g/L.

In one exemplary embodiment, the composition further comprises alkyl sulfonates in a concentration range of about 1.00 g/L.

In one exemplary embodiment, the composition comprises: sodium citrate dihydrate in a concentration of about 35 g/L; citric acid anhydrous in a concentration of about 33 g/L; sodium lauryl sulfate in a concentration of about 1 g/L; water; a total citrates in a concentration of about 63.83 g/L; and alkyl sulfonates in a concentration range of about 1.00 g/L, wherein a biofilm removing solution comprising the composition has a specific gravity in range of about 1.033 and has a pH value of about 3.93.

In one embodiment, the composition further comprises an antimicrobial ingredient. In one embodiment, the antimicrobial ingredient comprises an antibiotic, a bleach and silver sulfadiazine. In one embodiment, the antimicrobial ingredient is selected from the group consisting of an antibiotic, a bleach and silver sulfadiazine.

In one embodiment, the composition specifically targets the biofilm structure to break it up and remove or allow deeper penetration of the antibiotics. This coupled with the simultaneous use of IP antibiotics results in significant improvement in bacteria kill. This may also reduce the virulence for any microorganisms surviving the antibiotic treatment and allow the immune system to more readily clear the infection.

FIGS. 3A, 3B, 4 and 5 show demonstrate efficacy of a biofilm removing solution comprising the composition of the present disclosure for removing biofilm on a PD catheter. For example, FIG. 3 shows a microscopy of *P. aeruginosa* biofilm on catheter material (silicone), wherein the biofilm on catheter material after the use of the biofilm removing solution comprising the composition of the present disclosure was completely removed (see FIG. 3B; Product X) as compared to the control (see FIG. 3A; untreated).

Figure 4:
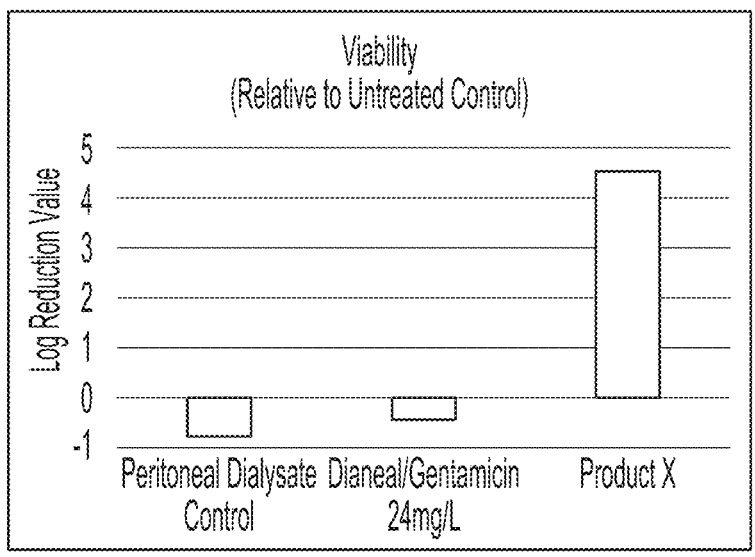
FIG. 4 is a graph showing the efficacy of a combination of sodium lauryl sulfate, sodium citrate, and citric acid, in aqueous solution (Product X) for biofilm removal.

FIG. 4 shows viable bacteria recovered from a catheter material after 6 hr treatment with the biofilm removing solution comprising the composition of the present disclosure.

Log reduction value (LRV) indicates removal of viable organisms. As shown in FIG. 4, the viable organisms were significantly removed after a 6 hr treatment with the biofilm removing solution comprising the composition of the present disclosure (Product X) as compared to the untreated control.

Figure 5:
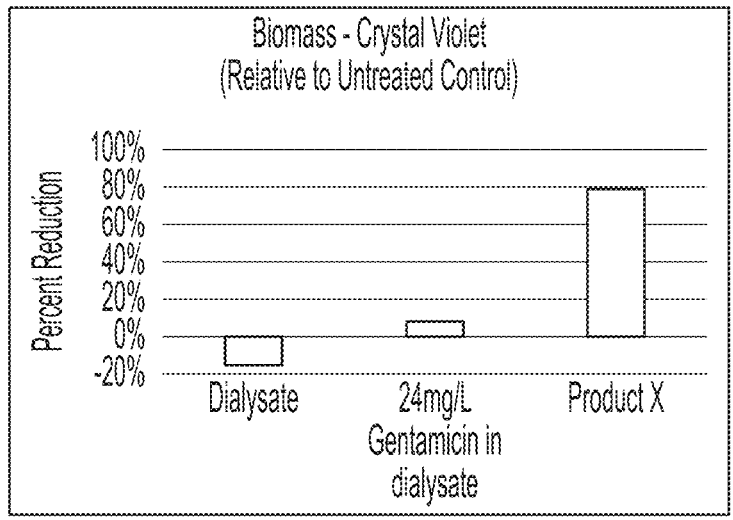
FIG. 5 is a graph showing the efficacy of a combination of sodium lauryl sulfate, sodium citrate, and citric acid, in aqueous solution (Product X) for biofilm removal.

FIG. 5 shows the biomass removal % relative to untreated control for *P. aeruginosa*, recovered from catheter material after 6 h treatment. As shown in FIG. 5, the biomass was significantly removed after a 6 hr treatment with the biofilm removing solution comprising the composition of the present disclosure (Product X) as compared to the untreated control.

The Methods

In an aspect, the present disclosure relates to a method of performing peritoneal dialysis (PD). Biofilms can form on surface of the PD catheters and the biofilms can be difficult to remove creating a reservoir for infectious microorganism leading to relapsing peritonitis, and potentially require catheter removal. The present disclosure provides a method to treat the inner lumen of the catheter to break up and remove biofilm on the catheter wall by using a biofilm removing solution as the biofilm removing solution (BRS). By disrupting the biofilm, the treatment can allow antibiotics used in standard peritonitis treatment to more effectively kill bacteria in the catheter and prevent relapsing peritonitis, or help prevent the occurrence of peritonitis. In one embodiment, the present disclosure uses a prefilled syringe or a similar device to deliver the biofilm removing solution (i.e., the biofilm removal solution) to the inner lumen of the PD catheter. The biofilm removing solution then dwells, while PD fluid in the peritoneum is dwelling and gets flushed out with PD effluent drain. In one embodiment, the method of performing peritoneal dialysis (PD) comprises filling patient with PD fluid dosed with or without antibiotics, locking the PD catheter with the biofilm removing solution (the biofilm solution), dwelling and then draining patient, flushing everything out of the PD catheter including the biofilm microorganisms and biofilm matrix material.

FIG. 1 shows an exemplary PD catheter decontamination and biofilm removal according to some embodiments of the present disclosure. As shown in FIG. 1, one end of a permanent PD catheter 1 is inserted into the peritoneal cavity 2 of a patient 3. The other end of the permanent PD catheter 1 is connected to a transfer set 9. Through the PD catheter 1, an antibiotic-containing PD fluid 4 is delivered into the peritoneal cavity 2 of the patient 3. Once a biofilm removing solution (i.e., a biofilm-removing solution) comprising the present composition is injected via a syringe 5 through the transfer set 9 and the PD catheter 1 and dwells within the transfer set 9 and the PD catheter 1 for a sufficient amount of time (e.g., 6 hours), the biofilm attached to the inner wall (and external wall) of the PD catheter 1 was removed. Numeral 6 shows an example of the inner wall the PD catheter 1 with biofilm 8 and numeral 7 shows the example of the inner wall the PD catheter 1 without biofilm after the PD catheter 1 is injected with the biofilm-removing solution comprising the present composition.

FIG. 1 shows an exemplary PD catheter decontamination and biofilm removal where the biofilm removing solution (i.e., the biofilm-removing solution) is injected through and dwells within the transfer set 9 and the PD catheter 1 after the antibiotic-containing PD fluid 4 is delivered (gravity or pumping) into the peritoneal cavity 2 of the patient 3.

In one embodiment, the biofilm removing solution of the present disclosure may be injected through and dwell within the transfer set and the PD catheter before, after or at the same time when the antibiotic-containing PD fluid is filled into the peritoneal cavity of the patient. In one exemplary embodiment, the biofilm removing solution of the present disclosure may be injected through and dwell within the transfer set and the PD catheter after the antibiotic-containing PD fluid is filled into the peritoneal cavity of the patient.

In one embodiment, the method of performing peritoneal dialysis (PD) comprises delivering a PD fluid to the peritoneal cavity of a patient through a PD catheter; dwelling the PD fluid within the peritoneal cavity; and while dwelling the PD fluid, removing a biofilm from the PD catheter wall using a biofilm removing solution.

As shown in FIG. 1, a PD fluid 4 may be delivered through a transfer set 9 and a PD catheter 1. The transfer set 9 connects to one end of the PD catheter 1 and the other end of the PD catheter 1 is inserted into the peritoneal cavity 2 of a patient 3. Thus, the PD fluid 4 may be delivered through a transfer set 9 and a PD catheter 1 to the peritoneal cavity 2 of a patient 3.

As shown in FIG. 1, once a PD fluid is delivered to the peritoneal cavity of a patient through a PD catheter, a pharmaceutically sufficient amount of the PD fluid 4 dwells within the peritoneal cavity 2 of the patient 3 for a first period of time. The pharmaceutically sufficient amount of the PD fluid 4 and the first period of time may be each independently determined on the basis of the age, weight, gender, seriousness of the disease and other factors of the patient 3.

As shown in FIG. 1, while the PD fluid 4 dwells within the peritoneal cavity 2 of a patient 3, a biofilm from the PD catheter wall is removed by using a biofilm removing solution.

In one embodiment, the biofilm removing solution may be injected by using a syringe through transfer set 9 and PD catheter 1. As shown in FIG. 1, the biofilm removing solution was injected by using a syringe 5 through the transfer set 9 and the PD catheter 1.

In one embodiment, the biofilm removing solution may be provided in a pre-filled syringe ready to use. In another embodiment, the biofilm removing solution may be provided in a sterile ampule, vial, or bag that may be later transferred to a syringe.

In one embodiment, the syringe has an adjustable setting to allow one to pre-set the volume delivered. The reason for the delivered variability is that on-market catheters vary significantly in volume (e.g. 3-15 mL) and providing a set volume is not possible. One may determine the suspected volume of the catheter, then pre-set the syringe accordingly to minimize overfill. For example, an adjustable stop that limits the amount that is able to be transferred to the syringe.

Figure 2:
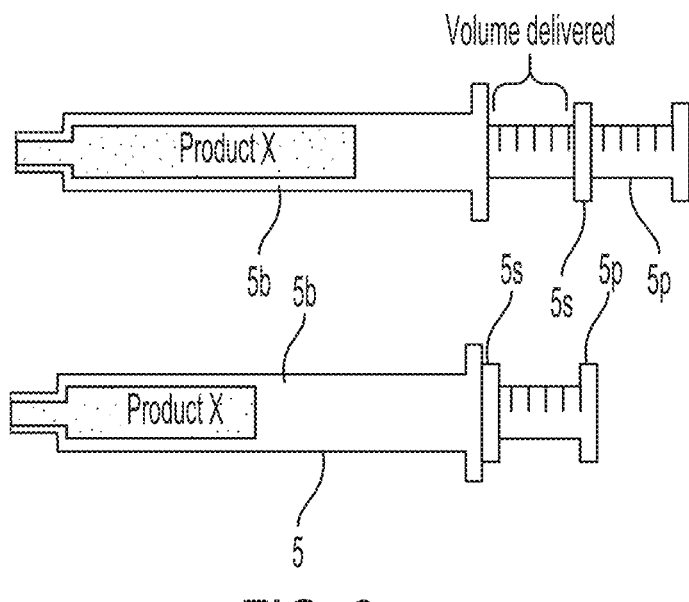
FIG. 2 is a set of diagrams showing another exemplary adjustable volume biofilm-removing solution delivering syringe 5 including a syringe barrel 5b and a syringe plunger 5p.
Figures 3A, 3B:
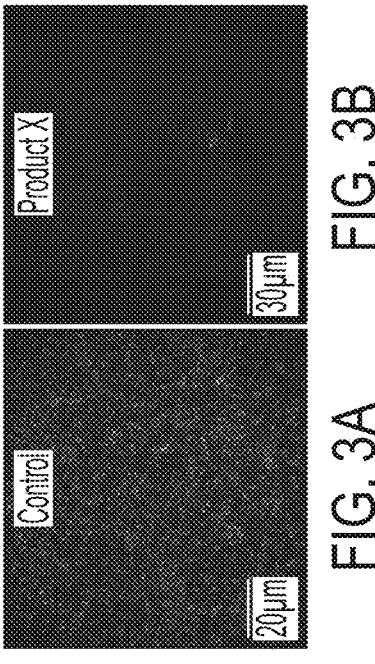
FIG. 3A and FIG. 3B are a set of images showing efficacy of a combination of sodium lauryl sulfate, sodium citrate, and citric acid, in aqueous solution (termed Product X) for biofilm removal.

In one embodiment, the adjustable clamp or stop 5s may be a clamped or threaded ring on to the shaft of plunger 5p of syringe 5, as depicted in FIG. 2. As shown in FIG. 2, the shaft of plunger 5p of syringe 5 may be graduated so that one can set with the stop of the amount of delivered solution either after drawing the fluid into syringe 5, or upon receiving a pre-filled syringe 5. In one embodiment, the solution may be delivered via connection to a bag via pumping or gravity instillation.

Syringe 5 may be a "Smart" syringe, which is capable of detecting when solution has reached the end of the catheter. For example, the "Smart" syringe could be achieved by acoustic, electrical, optical, or pressure transduction. In one embodiment, once the biofilm removing solution has reached the peritoneal dwell, this may initiate a change in a signal. A threshold to indicate the user should stop injecting the biofilm removing solution could be used and send a notification via an audible or visible indication, or just prevent further pushing of the biofilm removing solution in the PD catheter.

In one embodiment, the biofilm removing solution as discussed above comprises sodium citrate (e.g., sodium citrate dihydrate); citric acid (e.g., citric acid anhydrous); a surfactant (e.g., sodium lauryl sulfate); and water. In one exemplary embodiment, the biofilm removing solution as discussed above comprises sodium citrate dihydrate; citric acid anhydrous; sodium lauryl sulfate; and water.

In one embodiment, the biofilm removing solution as discussed above comprises sodium citrate dihydrate in a concentration range of about 32.13 g/L to about 39.27 g/L; citric acid anhydrous in a concentration range of about 29.25 g/L to about 35.75 g/L; sodium lauryl sulfate in a concentration range of about 0.95 g/L to about 1.05 g/L; and water.

In one embodiment, the biofilm removing solution further comprises: a pH value in the range of about 3.70 to about 4.10 (preferably, about 3.93); a total citrates in a concentration range of about 57.45 g/L to about 70.21 g/L (preferably, about 63.83 g/L); and a specific gravity in range of about 1.025 to about 1.042 (preferably, about 1.033). In one embodiment, the biofilm removing solution further comprises alkyl sulfonates in a concentration range of about 0.61 g/L to about 1.10 g/L (preferably, about 1.00 g/L). In another embodiment, the biofilm removing solution further comprises an antimicrobial ingredient selected from the group consisting of an antibiotic, a bleach and silver sulfadiazine.

In one embodiment, the transfer set 9 may include a transfer set valve, which is capable of stopping the flow of the biofilm removing solution so that the biofilm removing solution can dwell within the transfer set 9 and the PD catheter 1. In one embodiment, the biofilm removing solution can dwell within the transfer set 9 and the PD catheter 1 for a second period of time, which is sufficient for the removal of the biofilm on the inner wall and/or external wall of the transfer set and the PD catheter.

In one embodiment, the second period of time is in the range of about 0.1 hour to about 100 hours, about 0.5 hour to about 50 hours, about 1 hour to about 25 hours, about 1 hour to about 20 hours, about 1.5 hours to about 15 hours, about 2 hours to about 10 hours, about 3 hours to about 9 hours, about 4 hours to about 8 hours, about 5 hours to about 7 hours, or about 5.5 hours to about 6.5 hours.

In one embodiment, the third period of time is in the range of about 0.1 hour to about 20 hours, about 0.2 hour to about 15 hours, about 0.3 hour to about 10 hours, about 0.4 hour to about 5 hours, about 0.5 hours to about 4 hours, about 0.6 hours to about 3 hours, about 0.7 hours to about 2 hours, about 0.8 hours to about 1.9 hours, about 0.9 hour to about 1.9 hours, about 1.0 hour to about 1.8 hours, about 1.1 hours to about 1.7 hours, about 1.2 hours to about 1.6 hours, about 1.3 hours to about 1.55 hours, about 1.4 hours to about 1.54 hours, about 1.45 hours to about 1.53 hours, about 1.47 hours to about 1.52 hours, about 1.48 hours to about 1.51 hours, or about 1.5 hours.

In one embodiment, the second period of time is at or between about 1 hour and about 12 hours.

The method of performing peritoneal dialysis (PD) comprising removal of the biofilm on the inner wall and/or external wall of the transfer set and the PD catheter may be performed in any sequence as understood by the skilled artisan. For example, the biofilm removing solution of the present disclosure may be injected through and dwell within the transfer set and the PD catheter before, after or at the same time when the antibiotic-containing PD fluid is filled into the peritoneal cavity of the patient. In one exemplary embodiment, the biofilm removing solution of the present disclosure may be injected through and dwell within the transfer set and the PD catheter after the antibiotic-containing PD fluid is filled into the peritoneal cavity of the patient.

In one embodiment, the biofilm removing solution comprising the composition of the present disclosure may be applied to both patients with an active infection (reactive), or to reduce the likelihood of infection.

In one embodiment, the biofilm removing solution comprising the composition of the present disclosure may be locked in the PD catheter after instillation of PD fluid with or without antibiotic. The biofilm removing solution instillation duration could correspond with typical intraperitoneal (IP) antibiotic treatment, which is typically around 6 h but dependent on facility protocols. The biofilm removing solution may also be applied after antibiotic treatment using a regular PD fluid dwell (e.g., Dianeal™ PD fluid).

In another embodiment, the biofilm removing solution comprising the composition of the present disclosure may be locked in the PD catheter after instillation of PD fluid at various frequencies. For example, once per month, once per clinic visit, once per transfer set change (typically every 6 months). This treatment could be particularly beneficial for patients prone to peritonitis. The treatment time may be adjusted to be more reasonable; for example, 1 hour to 6 hours (e.g., 1.5 hours) to match a typical dwell duration. However, efficacy may be reduced with shorter durations.

In one embodiment, the step of removing the biofilm from the PD catheter wall using the biofilm removing solution comprises: transferring the biofilm removing solution into a syringe; connecting the syringe to a transfer set of the PD catheter; and filling the transfer set and the PD catheter with the biofilm removing solution.

FIGS. 6A, 6B, 6C, 7A, 7B, 7C, 8A, 8B and 8C show an exemplary treatment sequence according some embodiments of the present disclosure. For example, FIGS. 6A, 6B, 6C, 7A, 7B, 7C, 8A, 8B and 8C show an example wherein the biofilm removing solution of the present disclosure may be injected through and dwell within transfer set 9 and PD catheter 1 after the antibiotic-containing PD fluid is delivered (gravity or pumping) into peritoneal cavity 2 of the patient.

Figures 6A, 6B, 6C:
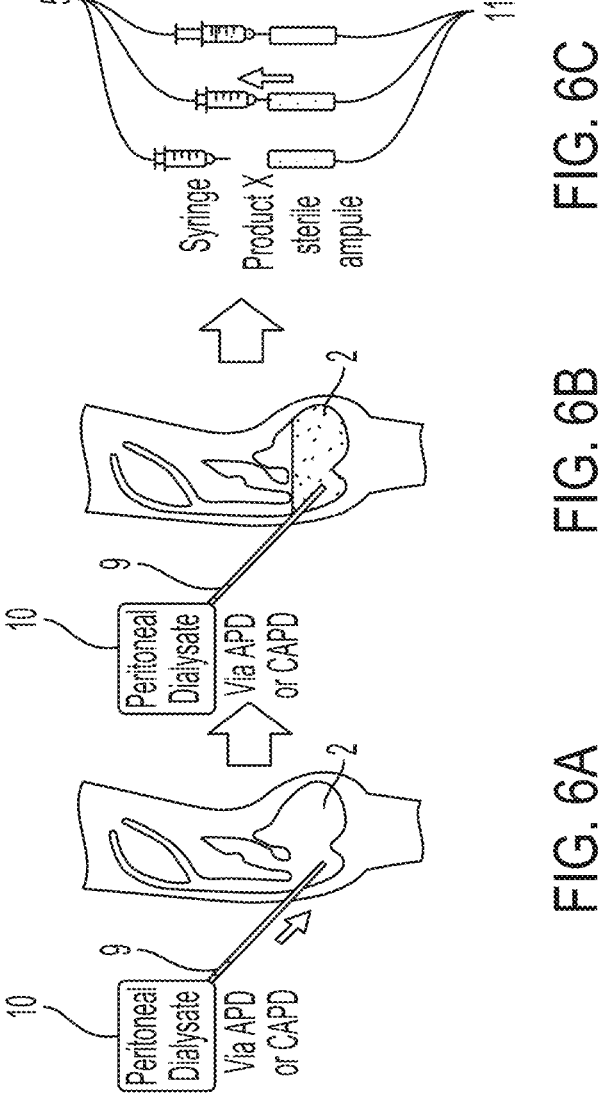
FIGS. 6A, 6B, 6C, 7A, 7B, 7C, 8A, 8B and 8C are a set of diagrams showing an exemplary treatment sequence according some embodiments of the present disclosure. For example.

Specifically, FIGS. 6A, 6B and 6C show the preparation of the peritoneal cavity 2 of a patient and a solution of the present disclosure before the treatment. As shown in FIG. 6A and FIG. 6B, to prepare the peritoneal cavity of the patient, the patient's peritoneal cavity 2 is filled with PD fluid through transfer set 9 and PD catheter 1. As shown in FIG. 6B, several treatment choices are available for patients considering PD: automated peritoneal dialysis (APD) and continuous ambulatory peritoneal dialysis (CAPD).

As shown in FIG. 6C, once the patient's peritoneal cavity 2 is filled with PD fluid through transfer set 9 and the PD catheter 1 and the patient is undergoing treatment, a biofilm removing solution is prepared. For example, as shown in FIG. 6C, a biofilm removing solution is transferred from a sterile ampule to a 10-20 mL syringe with Luer connector.

In one embodiment, the biofilm removing solution may be provided in a pre-filled syringe ready to use. In another embodiment, the biofilm removing solution may be provided in a vial, or bag that may be later transferred to a syringe.

In one embodiment, the step of removing the biofilm from the PD catheter wall using the biofilm removing solution further comprises: closing transfer set valve to keep the biofilm removing solution in the transfer set and the PD catheter for a first period of duration. In one embodiment, the first period of time is about 6 hours.

Figures 7A, 7B, 7C:
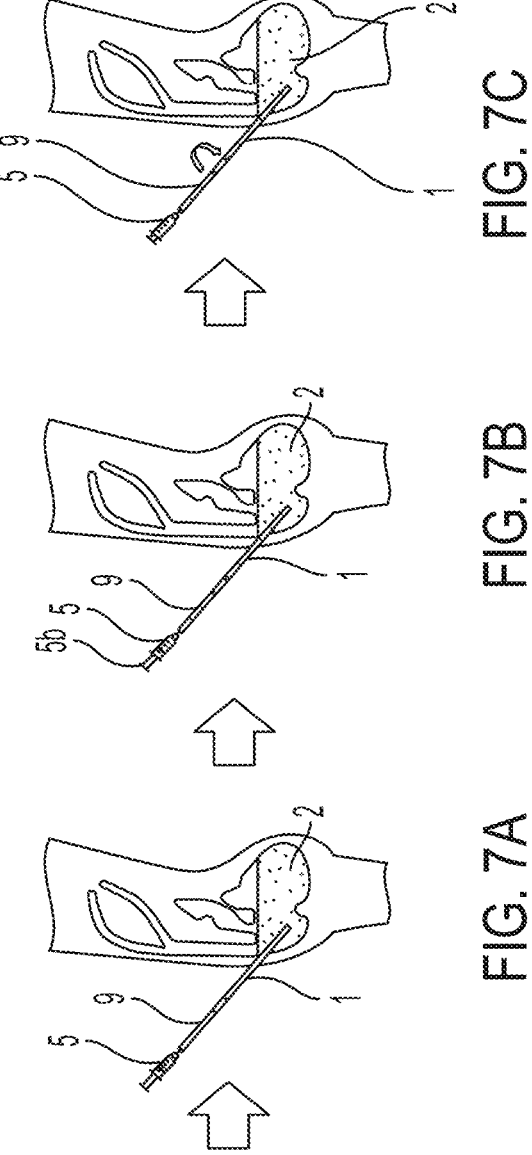

Referring to FIGS. 7A, 7B and 7C, once the biofilm removing solution is prepared in a syringe 5, the biofilm removing solution is delivered into and dwells within in transfer set 9 and PD catheter 1.

As shown in FIG. 7A, the Luer-connect solution-containing syringe 5 is connected to transfer set 9 and the biofilm removing solution is delivered into and dwells in transfer set 9 and PD catheter 1. FIG. 7B shows that transfer set 9 and the PD catheter 1 are filled with a sufficient amount (e.g., 5-10 mL) of the biofilm removing solution.

In one embodiment, the transfer set valve comprises a twist-actuated valve, which once closed is capable of stopping the flow of the biofilm removing solution and keep the biofilm removing solution in the transfer set and in the PD catheter.

FIG. 7C shows that the valve of transfer set 9 is closed to keep the biofilm removing solution in the transfer set and in the PD catheter for a third period of time of dwelling.

In one embodiment, the third period of time is in the range of about 0.1 hour to about 100 hours, about 0.5 hour to about 50 hours, about 1 hour to about 25 hours, about 1 hour to about 20 hours, about 1.5 hours to about 15 hours, about 2 hours to about 10 hours, about 3 hours to about 9 hours, about 4 hours to about 8 hours, about 5 hours to about 7 hours, or about 5.5 hours to about 6.5 hours.

In one embodiment, the third period of time is in the range of about 0.1 hour to about 20 hours, about 0.2 hour to about 15 hours, about 0.3 hour to about 10 hours, about 0.4 hour to about 5 hours, about 0.5 hour to about 4 hours, about 0.6 hour to about 3 hours, about 0.7 hour to about 2 hours, about 0.8 hour to about 1.9 hours, about 0.9 hour to about 1.9 hours, about 1.0 hour to about 1.8 hours, about 1.1 hours to about 1.7 hours, about 1.2 hours to about 1.6 hours, about 1.3 hours to about 1.55 hours, about 1.4 hours to about 1.54 hours, about 1.45 hours to about 1.53 hours, about 1.47 hours to about 1.52 hours, about 1.48 hours to about 1.51 hours, or about 1.5 hours.

In one embodiment, the third period of time is about 6 hours. In one embodiment, the third period of time is sufficient for removal of the biofilm located on the inner walls of the transfer set and the PD catheter and on external walls of a portion of the PD catheter located within the patient's peritoneal cavity.

Once the removal of the biofilm on inner walls and (external wall portion) of the transfer set and the PD catheter, the biofilm removing solution, the biofilm and antibiotic-containing dwell can be removed by any method understood by the skilled artisan.

For example, in one embodiment, the biofilm removing solution, the biofilm and antibiotic-containing dwell may be removed by a syringe manually. In one embodiment, a hand syringe pull would permit higher shear stress than via gravity or a cycler, which may lead to better cleaning. In one embodiment, a clinician may drain catheter with syringe, and then finish the dwell drain with CAPD/APD.

In one embodiment, the step of removing a biofilm from the PD catheter wall using the biofilm removing solution further comprises removing the biofilm removing solution, the PD fluid and the biofilm.

In one embodiment, the step of removing the biofilm removing solution, the PD fluid and the biofilm comprises: replacing the syringe with appropriate fluid connection(s) to an effluent bag; and opening the transfer set valve to drain the biofilm removing solution and the PD fluid into the effluent bag via gravity or pumping, wherein the biofilm removing solution and the PD fluid comprise the biofilm removed from the transfer set and the PD catheter.

In one embodiment, the biofilm is removed from the inner wall of the transfer set and the PD catheter and the outside wall of a portion of the PD catheter located within the patient's peritoneal cavity.

Figures 8A, 8B, 8C:
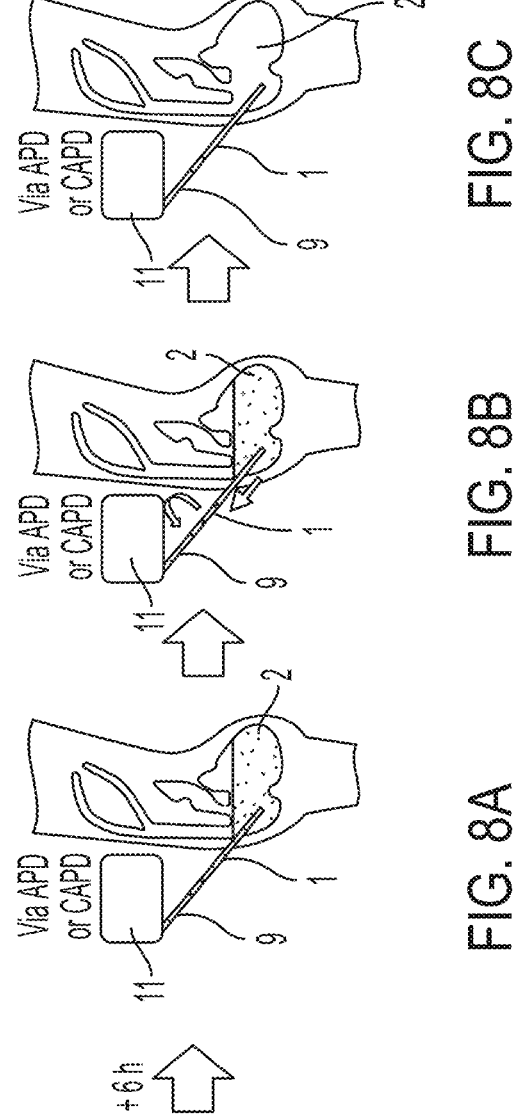

Referring now to FIGS. 8A, 8B and 8C, once the removal of the biofilm on inner walls and external walls of the transfer set and the PD catheter, the biofilm removing solution, the biofilm and antibiotic-containing dwell can be removed by e.g., effluent bag 11.

For example, FIG. 8A shows syringe 5 is replaced with appropriate fluid connection(s) to effluent bag (CAPD or APD). As shown in FIG. 8B, the valve of transfer set 9 is opened and that the draining of PD catheter 1 and the patient's peritoneal cavity 2 begins via gravity or pumping.

In one embodiment, the CAPD twin bag or and APD solution bag with the biofilm solution in the bag may be provided. For example, the biofilm removing solution may be infused into the patient through normal CAPD workflow or delivered by an APD cycler. The CAPD and APD bags may be pre-made or prepared by health care practitioner in the clinic.

In one embodiment, the post-dwell patient drain may remove the biofilm via shear stress. In one embodiment, normal instillation and drain settings may be used, but may potentially be increased to increase the shear stress at the surface of the catheter lumen where biofilm typically resides. Higher shear stress would presumably remove solubilized biofilm better or more quickly, but may be a trade-off with patient discomfort.

In one embodiment, pulsatile flow (most extreme case: start/stop) may be used to help break up the biofilm, and pulsatile flow may be enabled with use of a syringe, gravity, or a pump (e.g., via a PD cycler). For example, pulsatile shears of fluid may be applied in which the shear force is increased and decreased over different pulses to provide shear, mixing and potential disruption to the biofilm. For example, the cycler software may be used to generate more pronounced fluid flow pulsatility during drain.

FIG. 8C shows that the patient's peritoneal cavity 2 is drained and biofilm has been removed from the catheter and transfer set 9. The therapy/treatment may continue per facility protocol.

In one embodiment, one may fill the peritoneum with PD fluid first before locking the biofilm removing solution in the catheter. The purpose of this is to dilute any biofilm removing solution in several liters of PD fluid to minimize safety risk to patients. The biofilm removing solution could be administered with a variety of dwells, including those containing antibiotics intended to simultaneously treat the catheter with the biofilm removing solution while the peritonitis is treated. Alternatively, the dwell could be basic PD fluid (e.g., Dianeal™ PD fluid), possibly used after antibiotic treatment is over. The biofilm removing solution and the dwell could be drained either in-clinic or at the patient's home.

In one embodiment, the biofilm may be removed by using the biofilm removing solution in the catheter before antibiotic treatment.

In another embodiment, the biofilm may be removed by using a biofilm removing solution in the catheter after an antibiotic treatment.

In one embodiment, the transfer set may be kept attached during the biofilm removing solution treatment, removed, or replaced with a new transfer set. The transfer set itself may be used to valve/close during lock, or a valved line connected to the syringe or other delivery system may be used to lock. This additional valve or valve with additional tubing may be offered as part of the catheter decontamination product.

In some embodiments, the PD catheter may be flushed more than one time with the biofilm removing solution to aid in physical removal of the biofilm and microorganism.

The flushing may be performed manually or assisted with an automated pump. Other embodiments may mix antibiotics into the biofilm removal solution to provide both removal of biofilm and kill microorganisms, wherein the microorganisms may be either infectious microorganisms or non-infectious microorganisms. Another embodiment of the invention includes mixing the biofilm solution in the PD fluid, which would be infused into the peritoneum to remove biofilm on the outer wall of the catheter. Such embodiment may be particularly useful for APD, where the syringe may be more difficult to implement.

In one embodiment, the following additional options could improve the efficiency of the removal of the biofilm:

1. Increasing temperature during instillation or before instillation (e.g., pre-warming the solution) in the PD catheter could improve efficacy. A means to do this is to use a heated wrap or covering (like a heated blanket) to warm the catheter. Even a body temperature of 37°

C. could help with efficacy. In one embodiment, the solution may be pre-warmed.

2. Vibration during instillation in the PD catheter could improve efficacy. This is similar in function to sonicating a sample to remove from a surface, but would likely need to be applied in a more gentle manner. The trade-off would be patient discomfort and risk of inadvertent leaking of solution into the peritoneum. For example, sonic or ultrasonic energy may be used to improve biofilm removal. Ultrasonic energy is commonly applied to the human body without causing discomfort. Ultrasonic energy is also suitable for aiding in biofilm disruption.

3. A rinsing instill/drain cycle or cycles could be included after a workflow similar or the same as depicted in FIG. 2. For example, the peritoneum and catheter could be rinsed three times with PD fluid after use and draining of the biofilm removing solution. This could help in removing residual BRS or biofilm components that could remain in the peritoneum/catheter.

4. Mechanical forces beyond shear stress enacted on the biofilm could aid in its removal. For example, manual or motorized brushes could be used in conjunction with the biofilm removing solution to brush the lumen of the PD catheter.

An aspect of the present disclosure is a method for decontaminating a peritoneal dialysis (PD) catheter and removing a biofilm from the PD catheter and a transfer set.

The method comprises providing a biofilm removing solution; transferring the biofilm removing solution into a syringe; connecting the syringe to a transfer set of the PD catheter; and filling the transfer set and the PD catheter with the biofilm removing solution.

In one embodiment, the method further comprises closing transfer set valve to keep the biofilm removing solution in the transfer set and the PD catheter for a first period of duration.

In one embodiment, the first period of time is about 6 hours.

In one embodiment, the first period of time is between about 0.5 hour and about 12 hours.

In one embodiment, the first period of time is between about 0.5 hour and about 6 hours.

In one embodiment, the first period of time is between about 1 hour and about 2 hours.

In one embodiment, the first period of time is at least about 6 hours.

In one embodiment, the first period of time is at most about 6 hours.

In one embodiment, the method further comprises removing the biofilm removing solution, the PD fluid and the biofilm.

In one embodiment, the step of removing the biofilm removing solution, the PD fluid and the biofilm comprises: replacing the syringe with appropriate fluid connection(s) to an effluent bag; and opening the transfer set valve to drain the biofilm removing solution and the PD fluid into the effluent bag via gravity or pumping, wherein the biofilm removing solution and the PD fluid comprise the biofilm removed from the transfer set and the PD catheter.

In one embodiment, the biofilm is removed from both inner wall of the transfer set and the PD catheter and outside wall the PD catheter within the patient's peritoneal cavity.

In one embodiment, the biofilm removing solution as discussed above comprises: sodium citrate dihydrate; citric acid anhydrous; sodium lauryl sulfate; and water.

In one embodiment, the citric acid attaches to and removes metallic bonds of extracellular polymeric substances secreted by microorganisms to thus remove the extracellular polymeric substances of the biofilm.

In one embodiment, the citric acid prevents further cross-link formation.

In one embodiment, the biofilm removing solution comprises: sodium citrate dihydrate in a concentration range of about 32.13 g/L to about 39.27 g/L; citric acid anhydrous in a concentration range of about 29.25 g/L to about 35.75 g/L; sodium lauryl sulfate in a concentration range of about 0.95 g/L to about 1.05 g/L; and water.

In one embodiment, the biofilm removing solution further comprises: a pH value in the range of about 3.70 to about 4.10; a total citrates in a concentration range of about 57.45 g/L to about 70.21 g/L; and a specific gravity in range of about 1.025 to about 1.042.

In one embodiment, the biofilm removing solution further comprises: alkyl sulfonates in a concentration range of about 0.61 g/L to about 1.10 g/L.

In one embodiment, the biofilm removing solution further comprises an antimicrobial ingredient.

In one embodiment, the antimicrobial ingredient is selected from the group consisting of an antibiotic, a bleach and silver sulfadiazine.

Figures 10A, 10B:
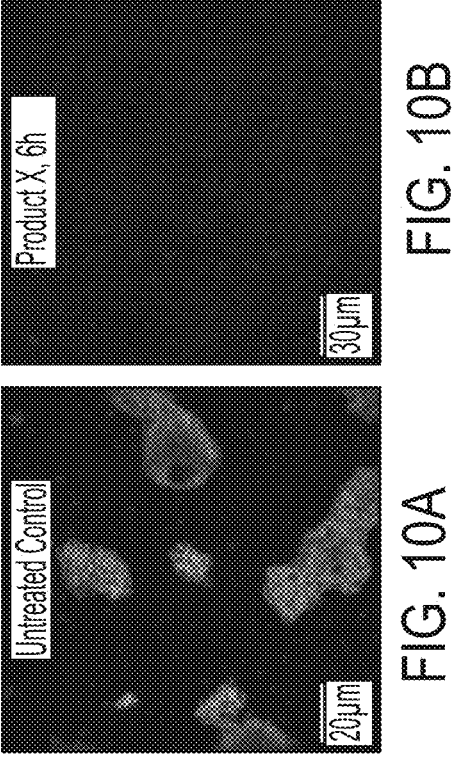
FIGS. 10A and 10B is a set of images showing efficacy of a biofilm removing solution comprising Sodium Citrate (35 g/L), Citric Acid (33 g/L), Sodium Lauryl Sulfate (1 g/L) in water at pH=4.

FIGS. 10A and 10B show efficacy of the biofilm removing solution comprising Sodium Citrate (35 g/L), Citric Acid (33 g/L), Sodium Lauryl Sulfate (1 g/L) in water at pH=4. For example, FIGS. 10A and 10B show removal of biofilm and viable bacteria by using the biofilm removing solution. As shown in FIG. 10B, the biofilm was removed or substantially removed after the wash of the biofilm removing solution (i.e. Product X) for 6 hours as compared to the untreated control without the wash of the solution (FIG. 10A).

Figure 11:
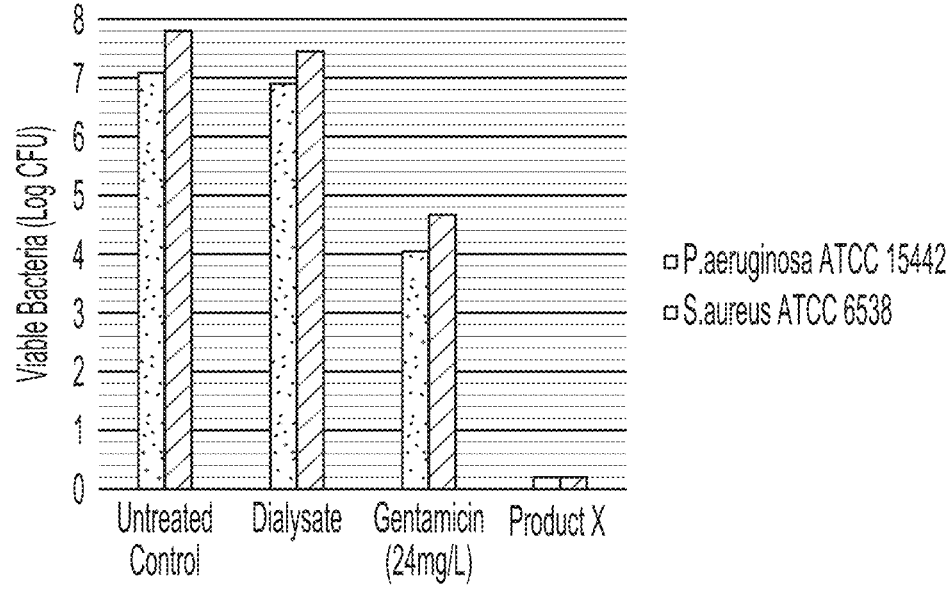
FIG. 11 is a set of graphs showing that the removing solution of the present disclosure is superior to antibiotics in removing bacteria.

FIG. 11 shows that the biofilm removing solution of the present disclosure is superior to antibiotics in removing bacteria. Specifically, FIG. 11 shows removal of biofilm from silicone. As shown in FIG. 11, no viable bacteria (e.g., *P. aeruginosa* ATCC 15442 and *S. aureus* ATCC 6538) were recovered after treatment with the biofilm removing solution (i.e., the Product X solution).

An aspect of the present disclosure includes a method of removing at least a portion of a biofilm present in the lumen of an indwelling peritoneal catheter while performing peritoneal dialysis therapy, the method comprising: delivering a dialysis fluid to the peritoneal cavity of a patient through the catheter; injecting a biofilm removing solution into the lumen of the catheter to occupy at least a portion of the lumen; dwelling the dialysis fluid within the peritoneal cavity; and removing the at least a portion of the biofilm removing solution from the catheter by withdrawing at least a portion of the dialysis fluid from the peritoneal cavity into the catheter.

EXAMPLES

The following non-limiting examples present scientific data developing and supporting the concept of performing peritoneal dialysis (PD) and decontaminating a peritoneal dialysis (PD) catheter and removing a biofilm from the PD catheter and a transfer set by using a biofilm removing solution comprising sodium citrate dihydrate; citric acid anhydrous; a surfactant such as sodium lauryl sulfate; and water.

Example 1

A PD Biofilm Removing Solution

The PD Biofilm removing solution is a clear, colorless, aqueous solution containing water, citric acid, sodium citrate, and sodium lauryl sulfate (Table 1). The surfactant sodium lauryl sulfate contained within the solution helps to solubilize organic debris coating the lumen of the catheter, making that debris more susceptible to removal by the hydrodynamic shear generated as part of the normal dialysate draining process.

The PD Biofilm removing solution can be provided in sterile vials/pre-filled syringes. The PD Biofilm removing solution can be delivered into the catheter by the healthcare provider, after the patient is filled with fresh PD fluid as part of their normal PD therapy. The total fill volume of the PD Biofilm removing solution can be approximately 3-6 mL, consistent with the fill volumes of the most commonly used PD Catheters. After instillation, the distal end of the catheter can be sealed creating a pressure gradient that inhibits the PD Biofilm removing solution from leaving the catheter. The PD Biofilm removing solution can reside in the catheter for up to 6 hours and then be drained out of the catheter when the patient drains the dialysate, as part of the normal PD therapy process.

Some of the PD Biofilm removing solution may enter into the peritoneum through the fenestrations and tip of the catheter. However, any solution that enters the peritoneum would be greatly diluted by the dwelling fresh PD fluid (typically 1.5 L-3 L), thus the concentration of the PD Biofilm removing solution within the peritoneal cavity is expected to be low and have no effect on the peritoneum or other patient tissues. Animal biocompatibility studies can be performed to demonstrate patient safety at worst case concentrations expected within the peritoneum.

TABLE 1

| The PD Biofilm removing solution Composition | | |
| --- | --- | --- |
| Ingredient | Grade | Range (g/L) |
| Sodium citrate dihydrate (CAS No. 6132-04-3) | USP/NF | 32.13 to 39.27 |
| Citric acid anhydrous (CAS No. 77-92-9) | USP/NF | 29.25 to 35.75 |
| Sodium lauryl sulfate (CAS No. 151-21-3) | USP/NF | 0.95 to 1.05 |
| Water for Injection (CAS No. 7732-18-5) | USP | To final volume of 1 L |

CAS No. = Chemical Abstracts Service number;

NF = National Formulary;

USP = United States Pharmacopoeia.

TABLE 2

| The PD Biofilm removing solution Properties | |
| --- | --- |
| Substance or Parameter | Target (Range) |
| Appearance | Clear |
| pH | 3.93 (3.70 to 4.10) |
| Specific gravity | 1.033 (1.025 to 1.042) |
| Total citrates | 63.83 g/L (57.45 to 70.21 g/L) |
| (citric acid and sodium citrate) | |

TABLE 2-continued

| The PD Biofilm removing solution Properties | |
| --- | --- |
| Substance or Parameter | Target (Range) |
| Alkyl sulfonates | 1.00 g/L (0.61 to 1.10 g/L) |
| Sterility | Sterile (steam) |

Chemical, Physical or Biological Composition

Table 3 and Table 4 provide the solution composition and properties for the biofilm removing solution.

TABLE 3

| The PD Biofilm removing solution Composition | | |
| --- | --- | --- |
| Ingredient | Grade | Range (g/L) |
| Sodium citrate dihydrate (CAS No. 6132-04-3) | USP/NF | 32.13 to 39.27 |
| Citric acid anhydrous (CAS No. 77-92-9) | USP/NF | 29.25 to 35.75 |
| Sodium lauryl sulfate (CAS No. 151-21-3) | USP/NF | 0.95 to 1.05 |
| Water for Injection (CAS No. 7732-18-5) | USP | To final volume of 1 L |

CAS No. = Chemical Abstracts Service number;
NF = National Formulary;
USP = United States Pharmacopoeia.

TABLE 4

| The PD Biofilm removing solution Properties | |
| --- | --- |
| Substance or Parameter | Target (Range) |
| Appearance | Clear |
| pH | 3.93 (3.70 to 4.10) |
| Specific gravity | 1.033 (1.025 to 1.042) |
| Total citrates | 63.83 g/L (57.45 to 70.21 g/L) |
| (citric acid and sodium citrate) | |
| Alkyl sulfonates | 1.00 g/L (0.61 to 1.10 g/L) |

Table 5 provides information on the feasibility tests conducted for the PD Biofilm removing solution device. The feasibility studies indicate: 1) the PD Biofilm removing solution is able to solubilize the components of EPS, as demonstrated in a model alginate system; 2) the PD Biofilm removing solution is able to remove organic debris from catheter material (silicone); and 3) along with organic debris, the PD Biofilm removing solution is able to facilitate removal of microorganisms.

TABLE 5

| Feasibility Testing Results | | |
| --- | --- | --- |
| Title | Test Description | Results |
| Solubilization and removal of Alginate, a model for organic debris | Alginate, a naturally occurring polysaccharide gel, is an accepted model substrate that mimics the extracellular polymeric substance (EPS) component of organic debris. The dissolution of the alginate gel in the PD Biofilm removing solution was compared to normal saline to evaluate the ability of the PD Biofilm removing solution to solubilize and aid in the removal of debris. Briefly, gel beads of alginate were prepared using a standard method. Beads were incubated in either the PD Biofilm removing solution or normal saline for 5 min, and then isolated. The differences in weight pre- and post-incubation were compared to quantify the amount of alginate solubilized. | the PD Biofilm removing solution was more effective than saline in solubilizing alginate, highlighting the ability of the PD Biofilm removing solution to aid in the solubilization of a model of EPS. |

TABLE 5-continued

Feasibility Testing Results

| Title | Test Description | Results |
|---|---|---|
| Removal of organic debris from Catheter Material - Crystal Violet Assay | To better mimic the naturally occurring organic debris that may contaminate PD catheters, *S. aureus* and *P. aeruginosa* were grown on silicone coupons using a modified ASTM method (ASTM E3161). Coupons were incubated in the PD Biofilm removing solution or PD fluid (DIANEAL - 2.5% Dextrose) for a period of 6 h, gently washed, and compared to an untreated control. Overall biomass was quantified using a standard stain for biomass (crystal violet). | the PD Biofilm removing solution was more effective than PD fluid (DIANEAL - 2.5% Dextrose) in aiding in the solubilization and removal organic debris from PD catheter material (silicone coupons). |
| Removal of organic debris from catheter material - Fluorescent Microscopy | *S. aureus* and *P. aeruginosa* were grown and treated with biofilm removing solution or PD fluid (Dianeal ® - 2.5% Dextrose) as described above. Confocal fluorescent microscopy was used to visually inspect and quantify representative regions of interest to assess the ability of the PD Biofilm removing solution to aid in the solubilization and removal of organic debris. | Microscopy analysis of microorganisms grown on catheter material (silicone coupons) corroborated the results of the biomass removal assay and highlighted the ability of the PD Biofilm removing solution to aid in the removal of organic debris as compared to the PD fluid control. |
| Removal of Microorganisms from catheter material | To investigate the ability of the biofilm removing solution to aid in the removal of microorganisms, in addition to organic debris, the amount of bacteria remaining on silicone coupons after incubation with the PD Biofilm removing solution was compared to a PD fluid control. *S. aureus* and *P. aeruginosa* were grown on silicone coupons and incubated with the PD Biofilm removing solution or PD fluid (DIANEAL - 2.5% Dextrose) as outlined above. Coupons were then gently washed and compared to an untreated control. The amount of bacteria (Colony Forming Units, CFUs) remaining on the coupon were quantified using standard microbiology techniques. | There was a significant reduction in the amount of bacteria remaining on the silicone coupons after incubation with the PD Biofilm removing solution as compared to the fluid control. These data in combination with the biomass removal studies (above) suggest the PD Biofilm removing solution is acts to aid in the solubilization and removal of organic debris and microorganisms from PD catheter material. |

Example 2

Solution presentation: The biofilm removing solution (BRS) could be provided in a pre-filled syringe ready to use. Alternatively, BRS could be provided in a sterile ampule, vial, or bag that is transferred to a syringe. The syringe itself could have an adjustable setting to allow the clinician to pre-set the volume delivered. The reason for the delivered variability is that on-market catheters vary significantly in volume (e.g. 3-15 mL) and providing a set volume is not possible. The clinician may determine the suspected volume of the catheter, then pre-set the syringe accordingly to minimize overfill. For example, an adjustable stop that limits the amount that is able to be transferred to the syringe. The adjustable stop could be a clamped or threaded ring on to the plunger shaft, as depicted in FIG. 2. The plunger shaft could be graduated so that the clinician can set with the stop the amount of delivered solution either after drawing the fluid into the syringe, or upon receiving a pre-filled syringe. Additionally, the BRS could be delivered via connection to a bag via pumping or gravity instillation.

Additionally, a "Smart" syringe could be used to detect when the solution has reached the end of the catheter. This could be achieved by acoustic, electrical, optical, or pressure transduction. For example, once the biofilm removing solution has reached the peritoneal dwell, this may initiate a change in a signal. A threshold to indicate the user should stop injecting could be used and send a notification via an audible or visible indication, or just prevent further pushing of fluid in the catheter.

Solution composition: Several classes of surfactants could be used to reduce the formation or presence of bacteria biofilm. These include biosurfactants (rhamnolipids, fengycin, glycolipid, lipopeptide, etc.), synthetic (poloxamers and betaines) and natural (sodium lauryl/dodecyl sulfate, cetyl trimethyl ammonium bromide, etc.). Additionally, citrates like sodium citrate and citric acid may aid in chelating key metal ions to help break down the biofilm scaffold. The solution may also contain antimicrobial ingredients, like antibiotics, bleach, silver sulfadiazine, etc.

In cases where the BRS would yield high or low pH, the PD fluid dwell could include a buffer agent to reduce the impact once in the peritoneum.

Note that the BRS uses a combination of sodium lauryl sulfate, sodium citrate, and citric acid, in aqueous solution. Data demonstrating efficacy of this sourced solution is depicted in FIG. 3.

Treatment frequency: BRS could be applied to both patients with an active infection, or to reduce the likelihood of infection:

For example, the solution could be locked in the PD catheter after filling of PD fluid with or without antibiotic. The BRS instillation duration could correspond with typical intraperitoneal (IP) antibiotic treatment, which is typically around 6 h but dependent on facility protocols. The BRS solution could also be applied after antibiotic treatment using a regular PD fluid dwell (e.g., Dianeal™ PD fluid).

In another example, the solution could be locked in the PD catheter after instillation of PD fluid at some frequency. For example, once per month, once per clinic visit, once per transfer set change (typically every 6 months). This treatment could be particularly beneficial for patients prone to peritonitis. The treatment time could be adjusted to be more reasonable; for example, 1.5 h to match a typical dwell duration. However, efficacy may be reduced with shorter durations.

Workflow: There are several workflows that could be implemented. For safety, these would likely involve filling the peritoneum with PD fluid first before locking the BRS in the catheter. The purpose of this is to dilute any BRS in several liters of PD fluid to minimize safety risk to patient. The biofilm removing solution could be administered with a variety of dwells, including those containing antibiotics intended to simultaneously treat the catheter with biofilm removing solution while the peritonitis is treated. Alternatively, the dwell could be basic PD fluid (e.g., Dianeal™ PD fluid), possibly used after antibiotic treatment is over. The biofilm removing solution after the dwell may be drained either in-clinic or at the patient's home.

An example "reactive" workflow is depicted in FIGS. 6A, 6B, 6C, 7A, 7B, 7C, 8A, 8B and 8C. The workflow may not contain antibiotic to avoid complications in an uninfected patient.

Fluid circuit: Components present during the treatment offer a few options. For example, the transfer set could be kept attached during the BRS treatment, removed, or replaced with a new transfer set. The transfer set itself could be used to valve/close during lock, or a valved line connected to the syringe or other delivery system could be used to lock. This additional valve or valve with additional tubing could be offered as part of the catheter decontamination product.

Fill and drain: Normal patient fill and drain settings may be used, but could potentially be increased to increase the shear stress at the surface of the catheter lumen where biofilm typically resides. In one embodiment, sonication may be used during drain to improve biofilm removal. Higher shear stress would presumably remove solubilized biofilm better, but would be a trade-off with patient discomfort. Pulsatile flow (most extreme case: start/stop) could help break up the biofilm, and could be enabled with use of a syringe, gravity, or a pump (e.g. PD cycler). For example, the cycler software could be used to generate more pronounced fluid flow pulsatility during drain. APD pumping may be performed such that fresh and/or used PD fluid is pumped back and forth or waffled through the PD catheter and transfer set at certain times to increase contact time and fluid turbulence.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of performing peritoneal dialysis (PD), the method comprising:

delivering a PD fluid to a peritoneal cavity of a patient through a PD catheter;

dwelling the PD fluid within the peritoneal cavity; and while dwelling the PD fluid, removing a biofilm from a PD catheter wall using a biofilm removing solution, wherein the biofilm removing solution consists of:

sodium citrate dihydrate;

citric acid anhydrous;

an alkyl sulfonate; and water.

2. The method of claim 1, wherein the alkyl sulfonate is a metal sulfonate.

3. The method of claim 2, wherein the metal sulfonate is sodium lauryl sulfate.

4. The method of claim 3, wherein the biofilm removing solution has:

sodium citrate dihydrate in a concentration range of about 32.13 g/L to about 39.27 g/L;

citric acid anhydrous in a concentration range of about 29.25 g/L to about 35.75 g/L;

sodium lauryl sulfate in a concentration range of about 0.95 g/L to about 1.05 g/L; and water.

5. The method of claim 1, wherein the biofilm removing solution has a pH value in the range of about 3.70 to about 4.10;

a total citrates in a concentration range of about 57.45 g/L to about 70.21 g/L; and a specific gravity in range of about 1.025 to about 1.042.

6. The method of claim 1, wherein the alkyl sulfonate is in a concentration range of about 0.61 g/L to about 1.10 g/L.

7. A method of performing peritoneal dialysis (PD), the method comprising:

delivering a PD fluid to a peritoneal cavity of a patient through a PD catheter;

dwelling the PD fluid within the peritoneal cavity; and while dwelling the PD fluid, removing a biofilm from a PD catheter wall using a biofilm removing solution, wherein the biofilm removing solution consists of:

sodium citrate dihydrate;

citric acid anhydrous;

an alkyl sulfonate;

water; and an antimicrobial ingredient.

8. The method of claim 7, wherein the antimicrobial ingredient is selected from the group consisting of: an antibiotic, a bleach and silver sulfadiazine.

9. The method of claim 1, wherein the PD fluid further includes an antibiotic for treating bacteria exposed by the removed biofilm.

10. The method of claim 1, wherein the step of removing the biofilm from the PD catheter wall using the biofilm removing solution comprises:

transferring the biofilm removing solution into a syringe;

fluidly communicating the syringe with a transfer set located along the PD catheter; and filling the transfer set and the PD catheter with the biofilm removing solution.

11. The method of claim 10, wherein the step of removing the biofilm from the PD catheter wall using the biofilm removing solution further comprises:

closing a transfer set valve to keep the biofilm removing solution in the transfer set and the PD catheter for a first period of time.

12. The method of claim 11, wherein the first period of time is between about 1 hour and about 12 hours.

13. The method of claim 11, wherein the first period of time is between about 1 hour and about 1.8 hours.

14. The method of claim 11, wherein the first period of time is about 1.5 hours.

15. The method of claim 13, wherein the step of removing a biofilm from the PD catheter wall using the biofilm removing solution further comprises removing the biofilm removing solution, the PD fluid and the biofilm.

16. The method of claim 15, wherein the step of removing the biofilm removing solution, the PD fluid and the biofilm comprises:

replacing the syringe with appropriate fluid connection(s) to an effluent bag or other drain; and opening the transfer set valve to drain the biofilm removing solution and the PD fluid into the effluent bag or other drain via gravity or pumping, wherein the biofilm removing solution and the PD fluid comprise the biofilm removed from the transfer set and the PD catheter.

17. The method of claim 15, wherein the biofilm is removed from inner walls of the transfer set and the PD catheter and an outer wall of a portion of the PD catheter located within a patient's peritoneal cavity.

18. A method of performing peritoneal dialysis (PD), the method comprising:

pumping a PD fluid including a biofilm removing solution to a peritoneal cavity of a patient through a PD catheter;

dwelling the PD fluid including a biofilm removing solution within the peritoneal cavity; and while dwelling the PD fluid including a biofilm removing solution, removing a biofilm from the PD catheter wall via the biofilm removing solution, wherein the biofilm removing solution consists of:
sodium citrate dihydrate;
citric acid anhydrous;
an alkyl sulfonate; and
water.

19. The method of claim 18, wherein the PD fluid further includes an antibiotic for treating bacteria exposed by the removed biofilm.

20. The method of claim 18, wherein the alkyl sulfonate is sodium lauryl sulfate.

21. A method of removing at least a portion of a biofilm present in a lumen of an indwelling peritoneal catheter while performing peritoneal dialysis therapy, the method comprising:

delivering a dialysis fluid to a peritoneal cavity of a patient through the catheter;

injecting a biofilm removing solution into the lumen of the catheter to occupy at least a portion of the lumen;

dwelling the dialysis fluid within the peritoneal cavity; and removing at least a portion of the biofilm removing solution from the catheter by withdrawing at least a portion of the dialysis fluid from the peritoneal cavity into the catheter, wherein the biofilm removing solution consists of:
sodium citrate dihydrate;
citric acid anhydrous;
an alkyl sulfonate; and
water.

22. The method of claim 21, wherein the alkyl sulfonate is sodium lauryl sulfate.

* * * * *